United States Patent
Mihara

[19]

[11] Patent Number: 5,805,663
[45] Date of Patent: Sep. 8, 1998

[54] RADIATION IMAGING METHOD AND SYSTEM

[75] Inventor: Toshiro Mihara, Tokyo, Japan

[73] Assignee: Futec, Inc., Kagawa-Ken, Japan

[21] Appl. No.: 853,317

[22] Filed: May 8, 1997

[51] Int. Cl.⁶ ................................................. A61B 6/06
[52] U.S. Cl. ........................... 378/98.2; 378/21; 378/145
[58] Field of Search .................... 378/98.2, 98.8, 378/145, 147, 86, 62, 21, 22, 25

[56] References Cited

U.S. PATENT DOCUMENTS

| | | | |
|---|---|---|---|
| 1,865,441 | 7/1932 | Mutscheller | 378/145 X |
| 2,638,554 | 5/1953 | Bartow et al. | 378/147 |
| 4,010,370 | 3/1977 | LaMay | 250/366 |
| 4,433,427 | 2/1984 | Barnea | 378/146 |
| 4,625,323 | 11/1986 | Okaya | 378/145 X |
| 4,821,304 | 4/1989 | Danos | 378/86 |
| 5,008,911 | 4/1991 | Harding | 378/147 X |
| 5,204,887 | 4/1993 | Hayashida et al. | 378/145 X |
| 5,602,893 | 2/1997 | Harding | 378/147 X |

FOREIGN PATENT DOCUMENTS

| | | | |
|---|---|---|---|
| 0117175 | 8/1984 | European Pat. Off. | G01N 23/04 |
| 19515778 | 4/1995 | Germany | G01N 23/04 |
| 2084832 | 4/1982 | United Kingdom | G01N 23/04 |

OTHER PUBLICATIONS

Crawford, et al. Moving Beam Helical CT Scanning, *IEEE Transactions on Medical Imaging*, Apr. 1996, No. 2.

D'Amico et al., X–Ray Microtomography With Monochromatic Synchrotron Radiation (Invited), *Review of Scientific Instruments*, Jul. 1989, Part 2A.

*Primary Examiner*—David P. Porta
*Attorney, Agent, or Firm*—Volpe and Koenig, P.C.

[57] ABSTRACT

A radiation imaging system for an object comprises a convergence type radiation generating unit for producing radiations having a radiation bundle so that it converges onto a given location, a radiation sensor unit opposed to the radiation generating unit with the object interposed therebetween, a pinhole member placed between the object and the radiation sensor unit, and a signal processing unit for processing an output signal of the radiation sensor unit.

12 Claims, 17 Drawing Sheets

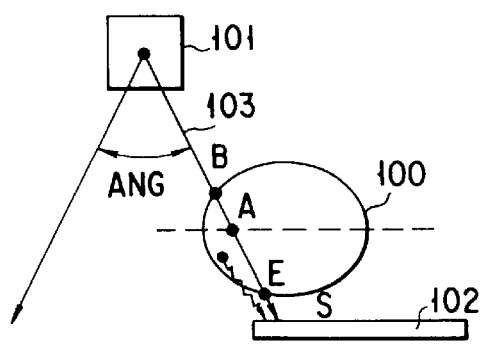
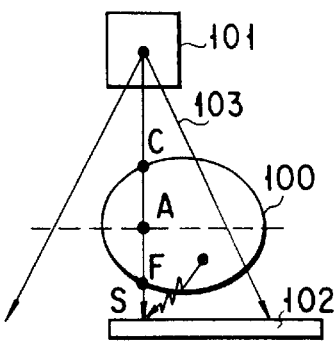
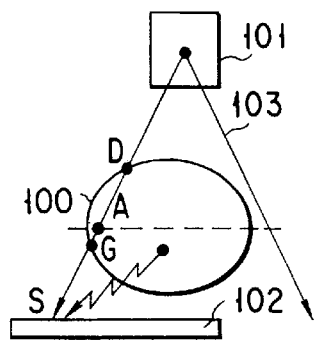
F I G. 2A    F I G. 2B    F I G. 2C
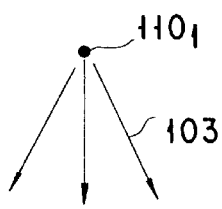
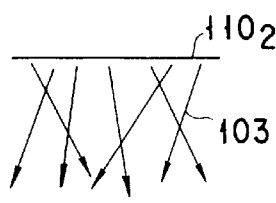
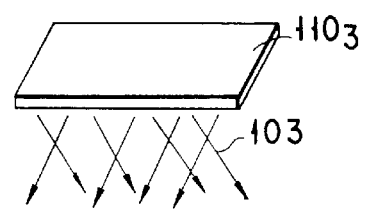
F I G. 3A    F I G. 3B    F I G. 3C
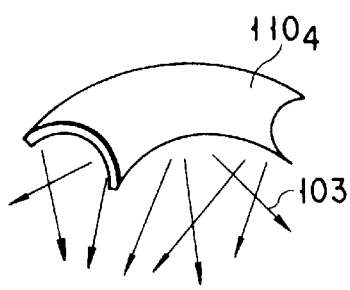
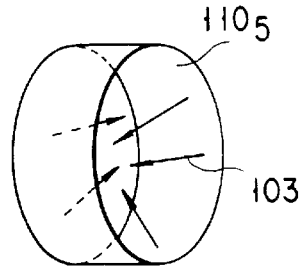
F I G. 3D    F I G. 3E

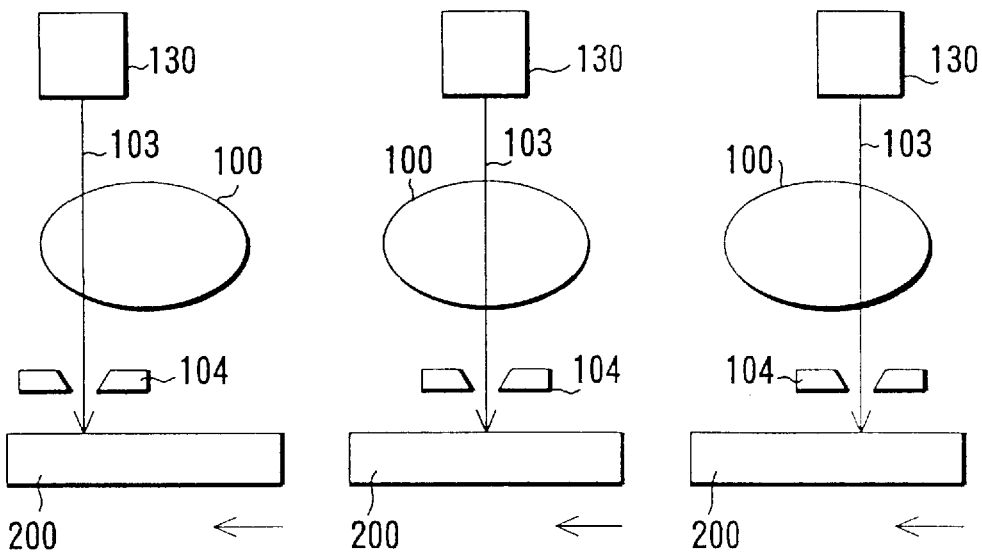
F I G. 11A    F I G. 11B    F I G. 11C
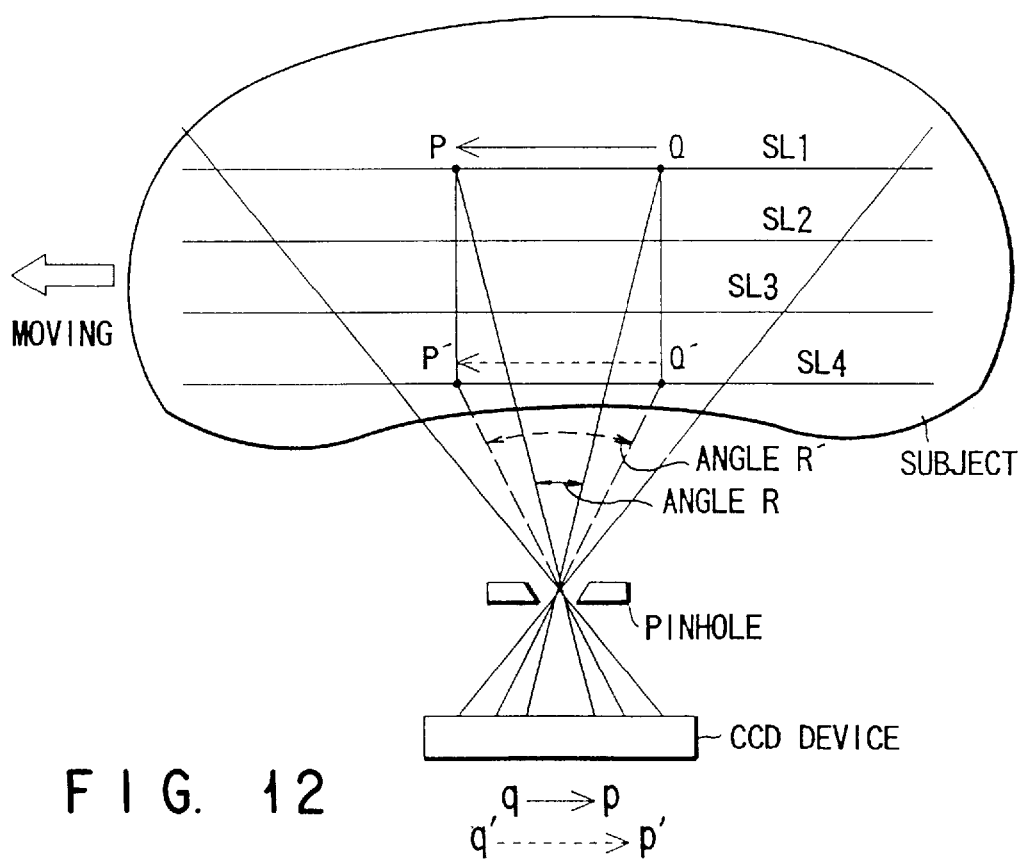
F I G. 12

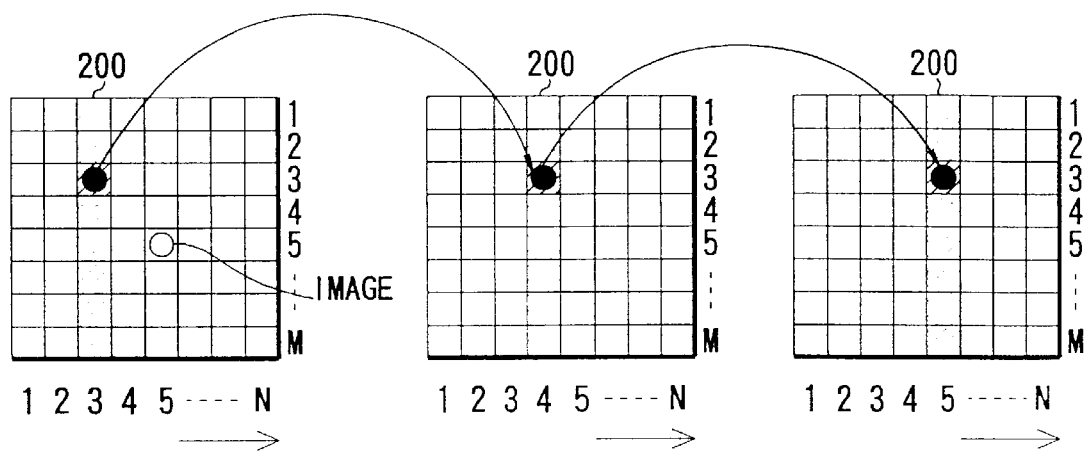
F I G. 13A   F I G. 13B   F I G. 13C
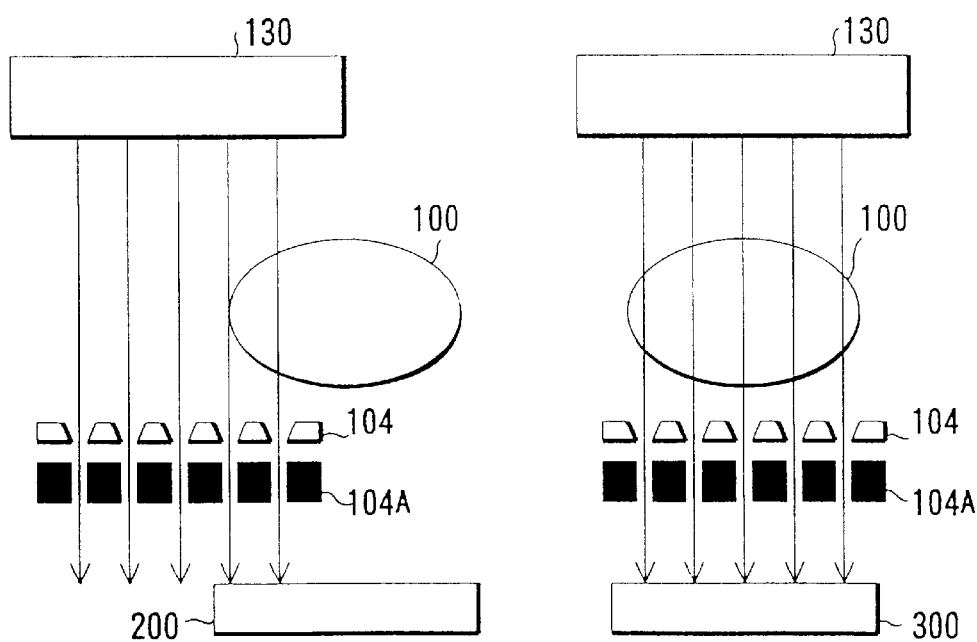
F I G. 14   F I G. 15

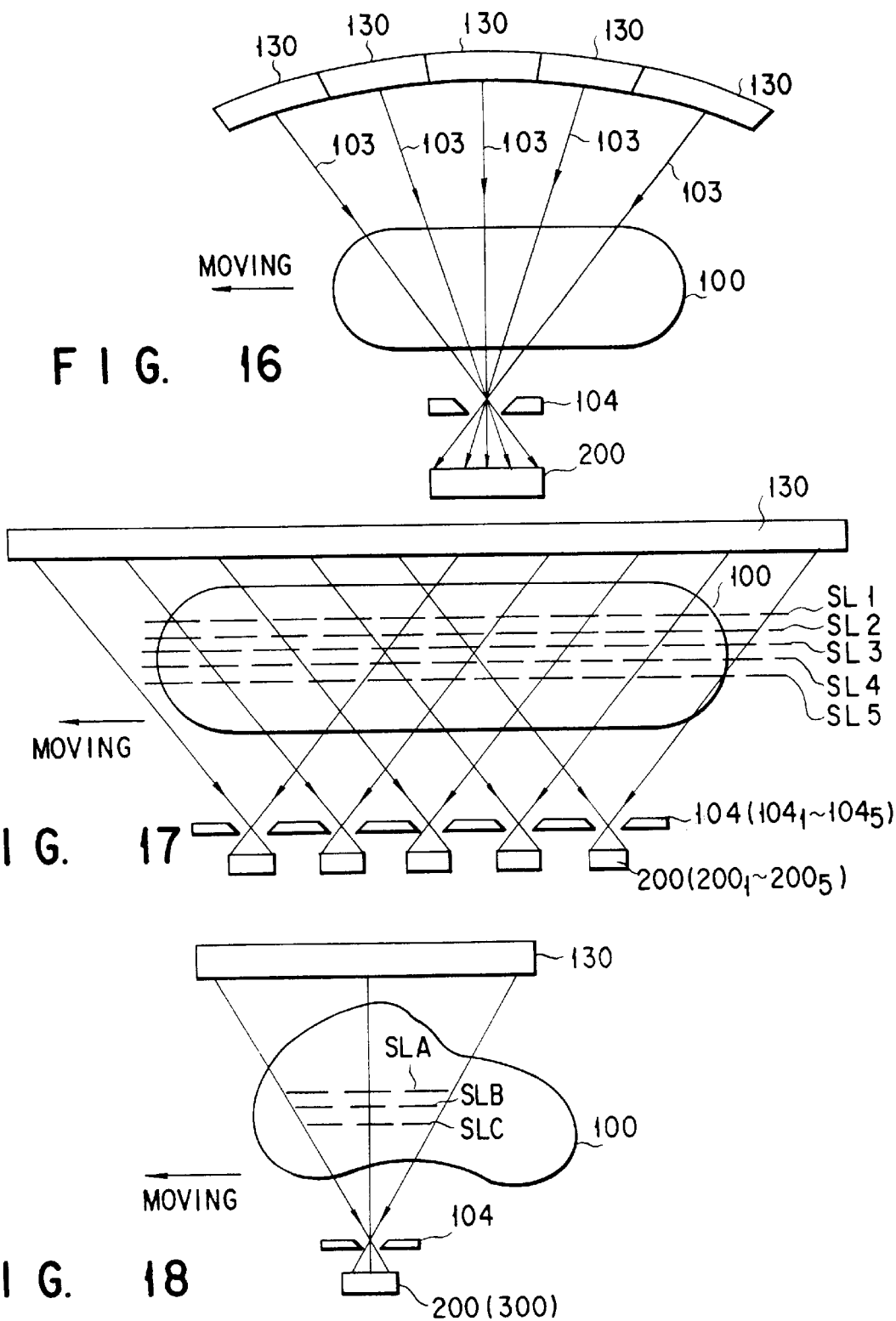

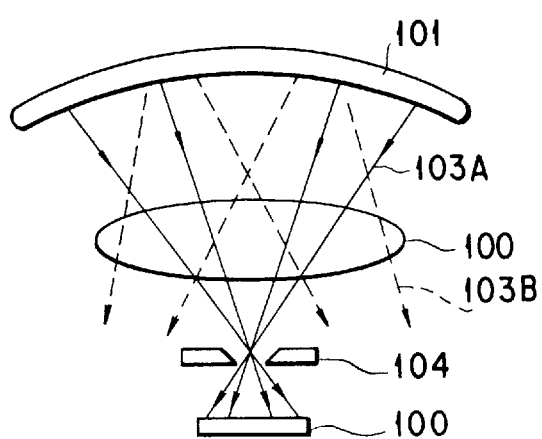
FIG. 21
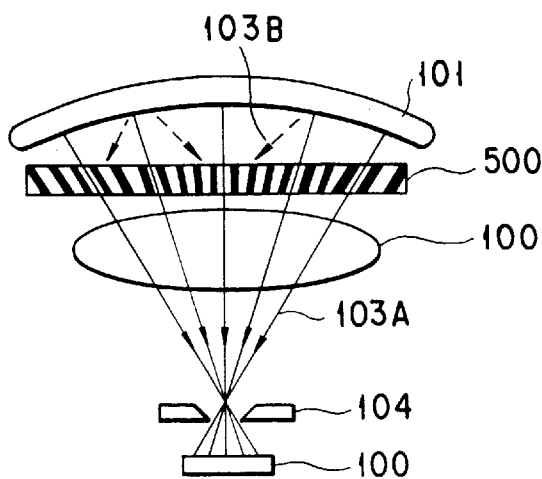
FIG. 22
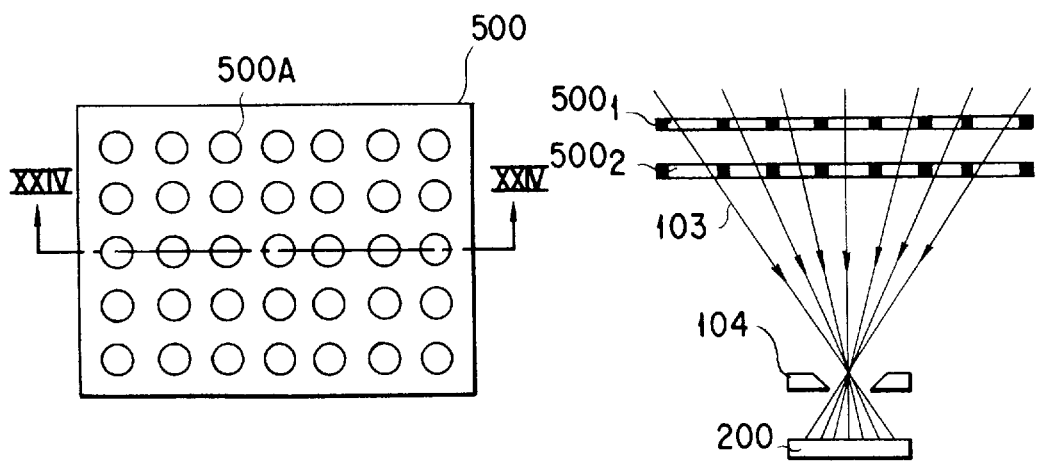
FIG. 23
FIG. 24

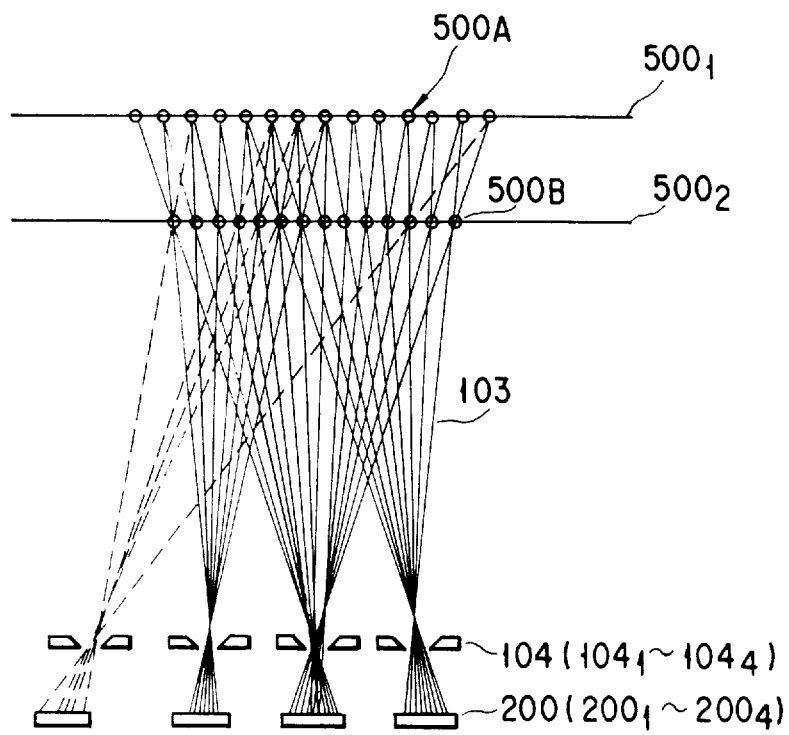
F I G. 25
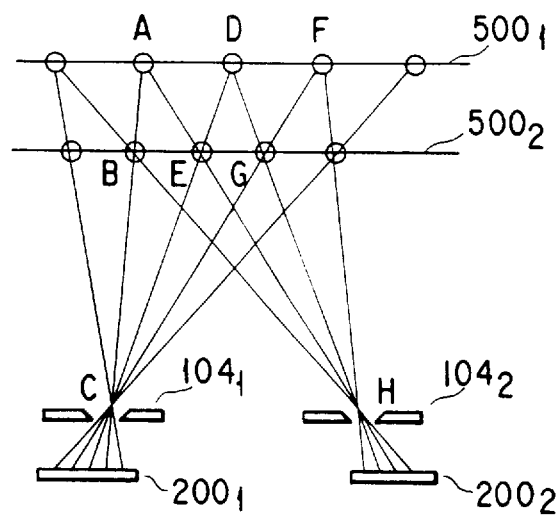
F I G. 26
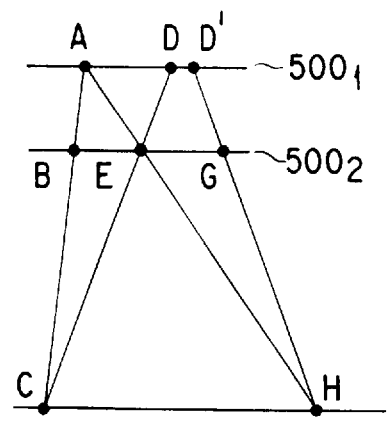
F I G. 27

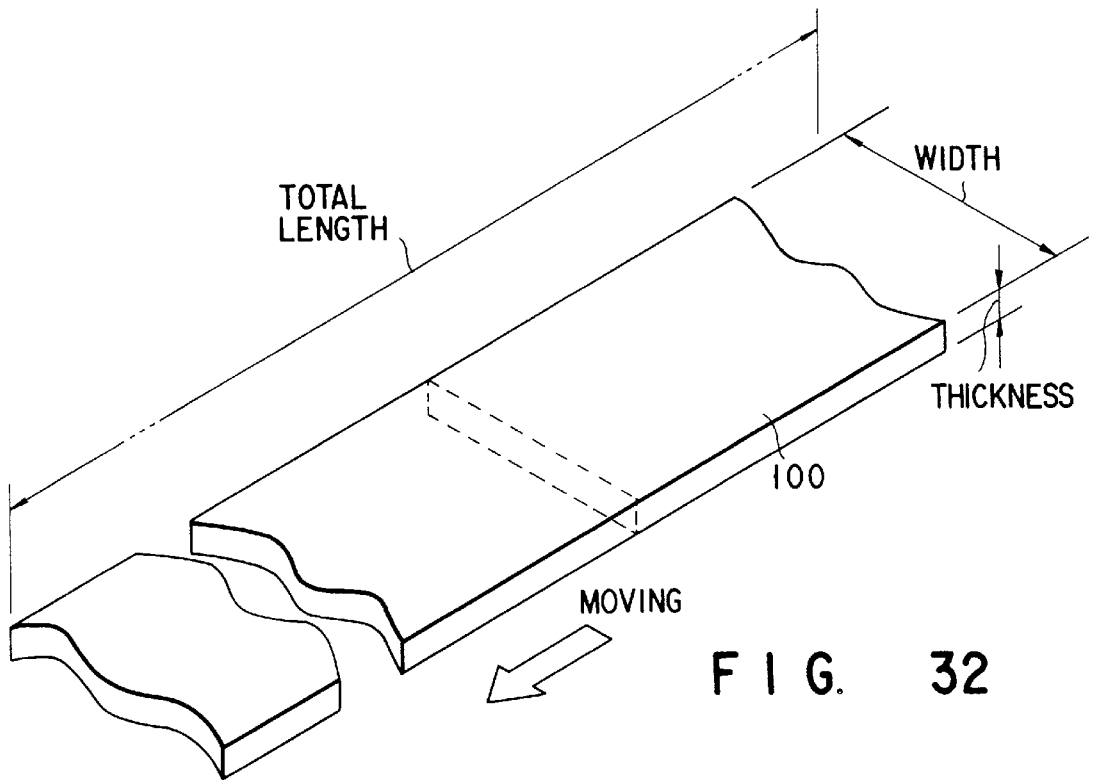
F I G. 32
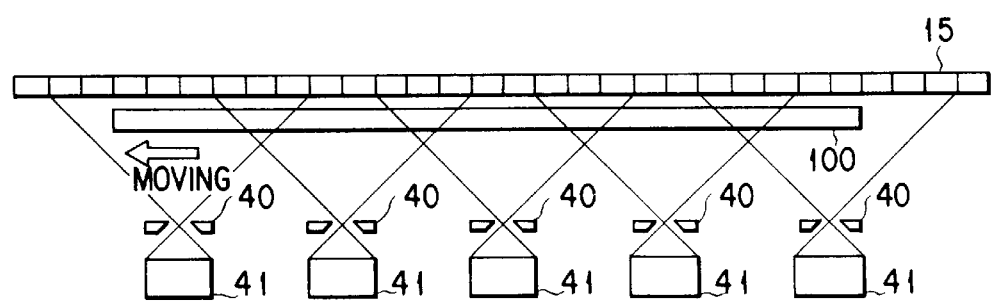
F I G. 33
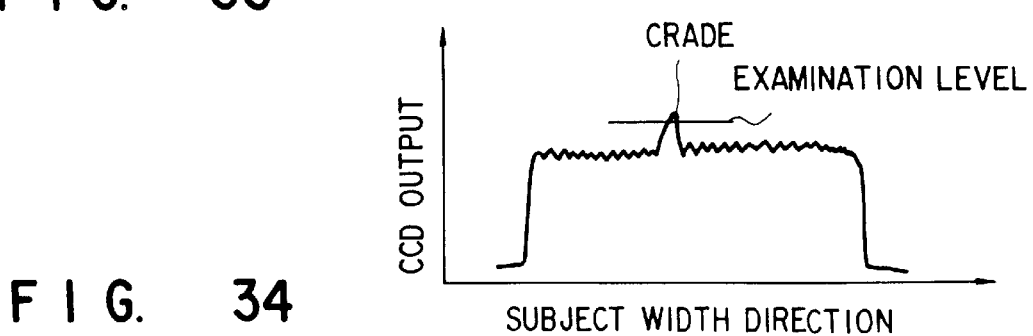
F I G. 34

RADIATION IMAGING METHOD AND SYSTEM

BACKGROUND OF THE INVENTION

The present invention relates to a method and system for imaging living or non-living objects with radiation, and more particularly to a radiation imaging method and system suitably adapted to tomography.

Radiation imaging method and system, typically X-ray imaging method and system, direct X-rays from an X-ray source onto an object under examination and visualize X-rays transmitted through the object using an X-ray film or an X-ray TV unit, etc.

X-ray images imaged by the X-ray film or X-ray TV unit, etc, include radiographs as a transmission X-ray image (simple X-ray transmission images) displayed by the X-ray film or TV monitor and tomographic images displayed by the TV monitor. Further, tomographic images include tomographic images produced by CAT (Computer-Assisted Tomography) and tomographic images produced by direct tomography. The former is implemented by an X-ray CAT scanner system, and the latter is formerly known as Laminargraphy or Planigraphy.

Problems to be solved with the radiation imaging method and system for producing X-ray images will be described below.

Firstly, in order to obtain clear X-ray images, it is required that the dimensions of the focus of the X-ray tube be small. However, the lower limit of the dimensions of the focus will be determined naturally because there is a limit on the thermal load of the target portion of the anode of the X-ray tube. That is, making the dimensions of the target small will lead to thermal degradation of the target. Desired dimensions of the focus cannot be obtained after all.

For a large object, the X-ray sensor must be large in area; otherwise, the entire object cannot be imaged at a time. Large X-ray sensors include photographic films. However, there is also a limit to the size of photographic films. Practically, the size of film is limited to the range of several centimeters regard to electronic or semiconductor type sensor to several tens of centimeters regard to vacuum type sensor. For this reason, an imaging method is desired which can image a large object at a time.

Secondly, it is difficult to obtain a large view of field. As the distance from the X-ray tube increases, the field of view becomes larger. It thus becomes possible to image a large object at a time. However, as the distance from the X-ray tube increases, the X-ray intensity becomes weaker. For this reason, it is impossible to place the object at a distance from the X-ray tube at which the practical sensitivity of the X-ray sensor cannot be obtained. Placing a plurality of X-ray tubes and a plurality of X-ray sensors to face each other would provide a large field of view. However, this will inconveniently produce dead space in the imaging field. Thus, with the conventional method, it is difficult to obtain a large view of field.

Thirdly, there is a phenomenon in which harmful scattered X-rays are imaged on a sensor, such as an X-ray film, an X-ray vidicon, a CCD image sensor, or an image intensifier. This phenomenon is the cause of a loss of visibility of images.

Fourthly, when the object is a human body, it is desired to decrease the amount of exposure to X-rays as much as possible. To decrease the amount of exposure, there is no effective means but decreasing the output of the X-ray tube. However, it is impossible to set the output of the X-ray tube at a lower level than the level required to obtain X-ray images.

Next, problems to be solved of the radiation imaging method and system for producing tomographic images will be described.

Firstly, it is desired to achieve a reduction of imaging time. That is, for tomographic imaging it is the heart, which exhibits the fastest motion in the body, that requires the fastest imaging. The human heart beats at intervals of about one second. When there is a need for serial tomographic images, it is desired to reduce the imaging time to about 1/10 of one second, or the heartbeat period. In producing tomographic images for industrial purposes, the imaging time needs to be further reduced. It is desired that images be displayed in real time, that is, the calculation time for imaging be zero. This is because, unlike human bodies, some industrial products are moved in succession at high speed on conveyers.

Secondly, it is required to produce tomographic images which are clear and free from unwanted scattered rays and image artifacts. That is, in producing tomographic images with X-ray CAT scanner, there arises the possibility of appearance of image artifacts and incomplete images, which may result in a failure of high-precision examination.

Thirdly, it is required to obtain multiple tomographic images fast and simultaneously.

Fourthly, it is required to obtain tomographic images with a sense of stereoscopy.

Fifthly, it is required to provide an imaging method and system which permit tomographic imaging and examination of a continuous object or serial objects.

Sixthly, it is required to provide an imaging method and apparatus in which objects are little exposed to radiation.

The object of the present invention is to provide a radiation imaging method and system for producing X-ray images and/or tomographic images of a living or non-living object which can solve one or more of the problems discussed above.

BRIEF SUMMARY OF THE INVENTION

According to the present invention there is provided a radiation imaging system for an object comprising: a convergence type radiation generating unit for producing radiations having a radiation bundle so that it converges onto a given location; a radiation sensor unit opposed to the radiation generating unit with the object interposed therebetween; a pinhole member placed between the object and the radiation sensor unit; and a signal processing unit for processing an output signal of the radiation sensor unit.

The system further comprising means for moving the radiation generating unit, the pinhole member, and the radiation sensor unit relative to the object.

In the system, the radiation sensor unit includes a storage type two-dimensional radiation sensor which has means for moving storage charges at a speed corresponding to the relative speed of movement of the object and the radiation sensor unit.

In the system, the convergence type radiation generating unit comprises a plurality of convergence type radiation generators that are arranged in parallel.

In the system, the radiation sensor unit includes a moving and storing type CCD arranged each that stored charges are moved and added, and means for moving storage charges in the moving and storing type CCD at a speed corresponding to the relative speed of movement of a specific plane section within the object and the moving and storing type CCD.

In the system, the signal processing system includes a highpass filter.

In the system, the pinhole member has a hole the diameter of which is set such that the convergence and divergence angles of radiation become 50 degrees or more.

In the system, the pinhole member and the radiation sensor unit are placed close to each other.

In the system, the pinhole member comprises a pinhole plate and a slit plate.

In system further comprising an alignment member interposed between the radiation generating unit and the object for suppressing exposure of the object to radiation that does not fall on the radiation sensor unit.

In the system, the alignment member includes first and second alignment plates which are arranged in parallel and have a large number of holes, the coordinates of the center of each hole in the second alignment plate being proportionally reduced or enlarged with respect to those of the corresponding hole in the first alignment plate.

A method of radiation imaging an object comprises the steps of: producing radiations having a radiation bundle so that it converges onto a predetermined point; irradiating the object with the radiation; sensing radiation passed through the object through a pinhole member; and processing a radiation detect signal.

Additional objects advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 2A, 2B and 2C show the principles of direct tomographic imaging;

FIGS. 3A through 3E show an X-ray generator;

FIGS. 11A, 11B and 11C show the relationship among the X-ray generator, the X-ray sensor, the pinhole member, and the object to be imaged in the system of the present invention;

FIG. 12 shows the relationship among the X-ray generator, the X-ray sensor, the pinhole member, and the object to be imaged in the system of the present invention;

FIGS. 13A, 13B and 13C show the method of driving an area type of image sensor in the present invention;

FIGS. 14 and 15 shows the relationship among the X-ray generator, the X-ray sensor, the pinhole member including a slit plate, and the object to be imaged in the system of the present invention;

FIG. 16 shows an embodiment of the invention in which multiple X-ray generators are placed;

FIGS. 17 and 18 show a method of obtaining multiple tomographic images in accordance with the present invention;

FIGS. 21 and 22 are diagrams for use in explanation of the function of an alignment member;

FIG. 23 is a plan view of the alignment member of FIG. 22;

FIGS. 24 to 27 are diagrams for use in explanation of the function of the alignment member;

FIG. 32 shows the steel slab of FIG. 31;

FIG. 33 shows the relationship among the X-ray generator, the X-ray sensor, the pinhole member including the slit plate, and the object to be imaged in the system of FIG. 31;

FIG. 34 is a diagram for use in explanation of the defect decision method in the system of FIG. 31.

DETAILED DESCRIPTION OF THE INVENTION

Figure 1:
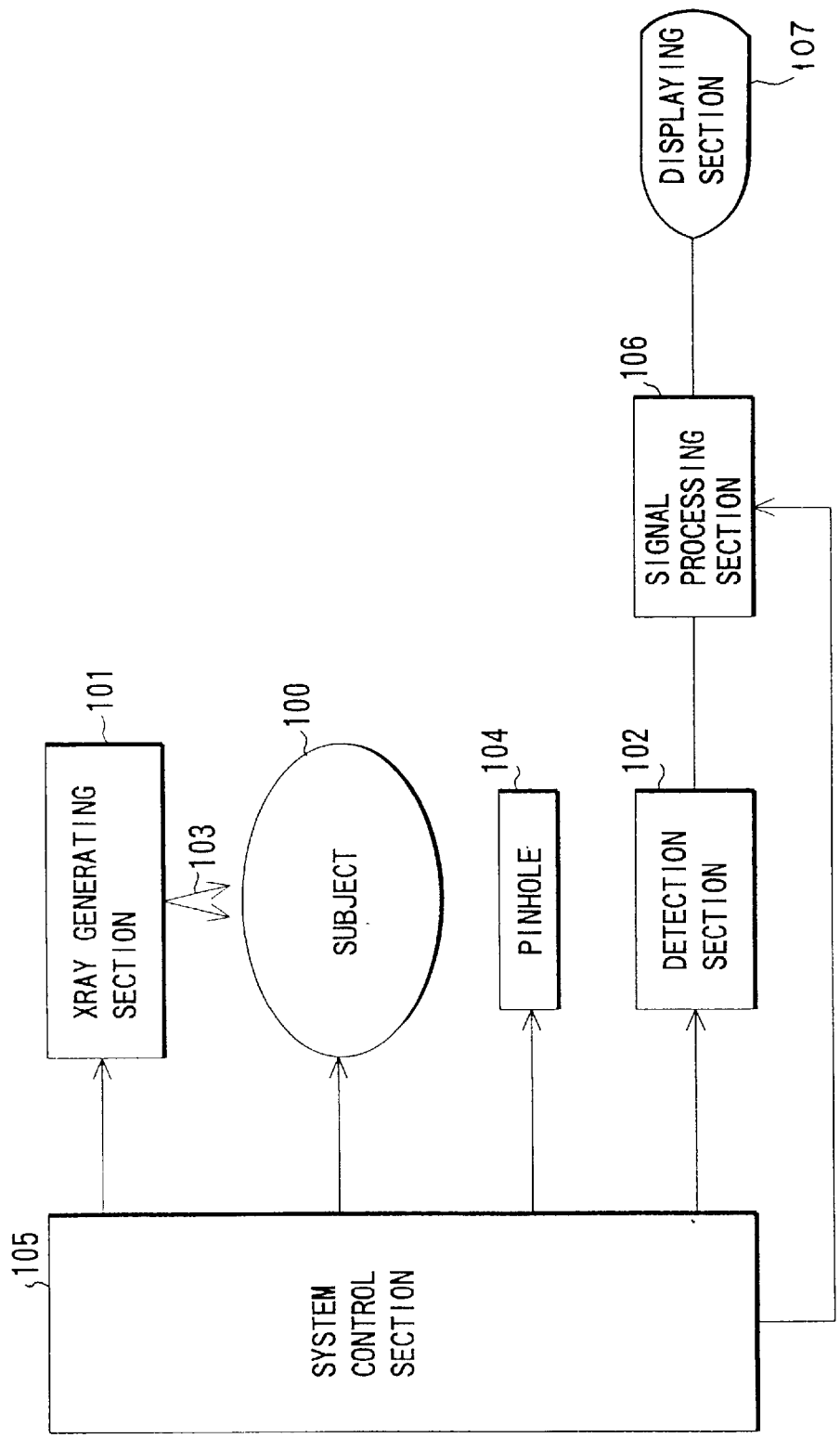
FIG. 1 is a block diagram of a radiation imaging system of the present invention.

The present invention is an imaging system in which, as shown in FIG. 1, an X-ray generator 101 and an X-ray sensor 102 are placed to face each other with an object 100 to be imaged interposed therebetween, and a pinhole member 104, serving as a space filter, is interposed between the object 100 and the X-ray sensor 102. In this system, the object 100 and the X-ray sensor 102 are moved with respect to each other for direct tomographic imaging. This relative motion is achieved by actually moving the object 100 and the X-ray sensor 102 or electrically controlling the X-ray sensor 102. A system controller 105 controls the movement of a couch on which the object 100 is placed, the operation of the X-ray generator 101, the movement and detecting operation of the X-ray sensor 102, and the operation of a signal processor 106 that processes output signals of the sensor 102. An output image produced by the signal processor 106 is displayed on a display unit 107.

Before describing the embodiments of the present invention, the principles of X-ray direct tomography using the imaging system of the present invention will be described with reference to FIGS. 2A, 2B, and 2C. As shown in these figures, X-rays 103 emitted from the X-ray tube 101 pass through the object 100 and reach a point S on the sensor 102 that is a storage type image sensor. If the travel speed of a specific slice SL1 of the object 100 and the travel speed of the sensor 102 are set equal to each other, then the positional relation among the X-ray tube 101, the object 100 and the sensor 102 will progress in time sequence as FIG. 2A→FIG. 2B→FIG. 2C.

In FIGS. 2A, 2B and 2C, let an arbitrary point on the specific slice SL1 be A. In FIG. 2A, the intensity of X-rays passing through the point A is stored at the point S on the sensor 103. Let the intensity be X1. Let typical points relating to the X-rays 103 be B, E, and A. Then, simplification can be made such that X1=B+A+E.

Likewise, X2=C+A+F in FIG. 2B, and X3=D+A+G in FIG. 2C.

Since the sensor 102 is a storage type image sensor, the stored intensity is represented by (X-ray intensity)=(X1)+(X2)+(X3).

$$\begin{aligned}\text{Thus, (X-ray intensity)} &= (B+A+E)+(B+C+D)+ \\ &\quad (D+A+G) \\ &= (A+A+A)+(B+C+D)+ \\ &\quad (E+F+G) \\ &= (3A)+(B+C+D)+ \\ &\quad (E+F+G)\end{aligned}$$

Although this expression is sufficient to obtain the theoretical concept of the direct tomography, it lacks mathematical strictness. Strictly, the absorption factor U of substance at each of points A, B, C, D, . . . is applied to the X-ray absorption expression I=Io EXP(–UT) where I is the X-ray intensity after transmission, Io is the X-ray intensity before transmission, and T is the thickness of the object 100.

If, in X-ray intensity (3A)+(B+C+D)+(E+F+G), it may be considered that A is weighted, and (B+C+D) and (E+F+D) are average backgrounds (background values), then (X-ray intensity)=(3A weighted)+(average background). If the average background is completely averaged background, then (X-ray intensity)=(3A weighted)=(A+A+A) according to human sense of vision. This is the principle of the direct tomography.

Next, the components of the present invention will be described. The storage type image sensor used in the present invention is one type of X-ray sensor in which traces of incoming X-rays are stored and added unless they are actively erased or transferred. Specific examples of storage type image sensors include photographic films, CCD image sensors, and light acceleration type imaging plates.

X-ray generators include divergent beam X-ray sources which diverge beams of X-rays at the prior art and convergent beam X-ray sources which make beams X-ray beams of an X-ray bundle converge at a specific point at the present invention. FIGS. 3A to 3E show various types of X-ray sources. FIG. 3A with the prior art shows a zero-dimensional X-ray source having an X-ray generating body of zero dimension (point) $110_1$, which is a divergent beam X-ray source.

FIG. 3B shows a one-dimensional X-ray source having a one-dimensional X-ray generating body (line) $110_2$, FIG. 3C shows a two-dimensional X-ray source having a two-dimensional X-ray generating body (plane) $110_3$, FIG. 3D shows a three-dimensional X-ray source having a three-dimensional X-ray generating body (curved surface) $110_4$, and FIG. 3E shows a three-dimensional X-ray source having a three-dimensional X-ray generating body (ring) $110_5$, which are all convergent beam X-ray sources. In the present invention, a convergent beam X-ray source can be used as the X-ray generator.

Figure 4:
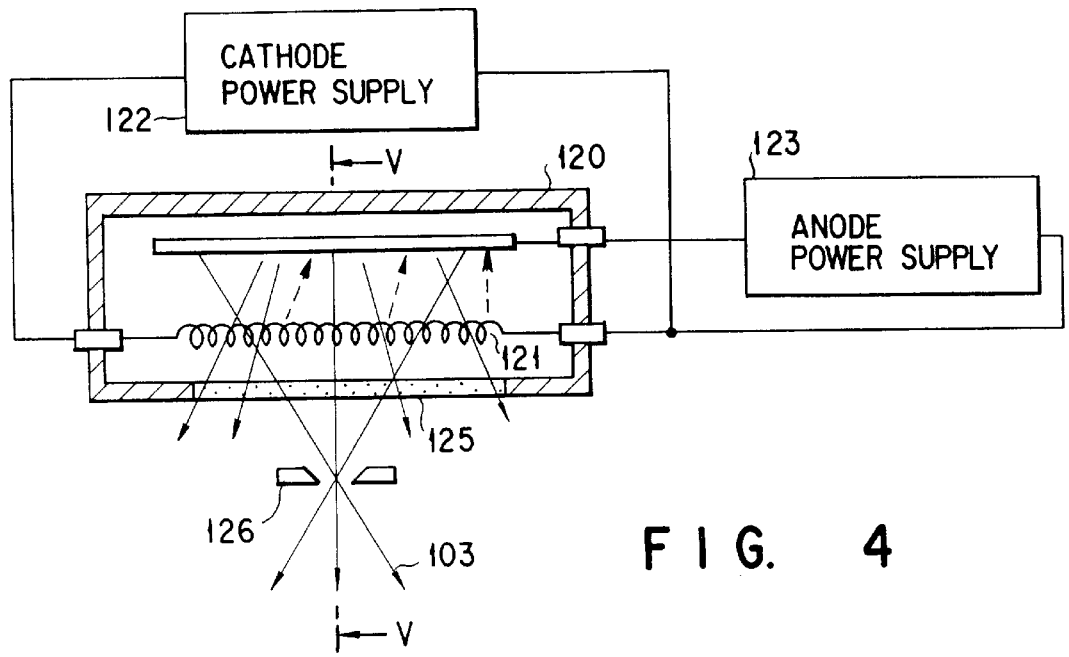
FIG. 4 shows a convergence type of two-dimensional X-ray generator of the present invention.
Figure 5:
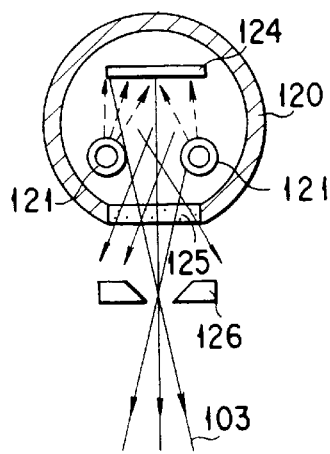
FIG. 5 is a sectional view taken along line V—V of FIG. 4.

FIGS. 4 and 5 are schematic illustrations of a convergent, two-dimensional type convergent beam X-ray generator that can be used in the present invention. In this X-ray generator, which is of the reflection type, two cathodes 121 are housed in a vacuum vessel 120 and heated by a cathode power supply 122 to emit thermoelectrons. The thermoelectrons are accelerated by an electric field produced by a high voltage applied by-an anode power supply 123 to an anode 124 and then bombard the anode 124, thereby emitting X-rays. In FIG. 4, the anode 124 doubles as a target. Part of X-rays thus produced transmit through an X-ray transmitting window 125 and a pinhole member 126.

Figure 6:
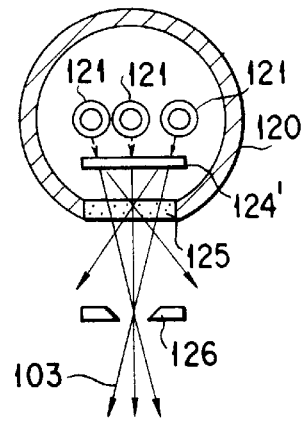
FIGS. 6 and 7 are sectional views of other embodiments of the convergence type of two-dimensional X-ray generator of the present invention.
Figure 7:
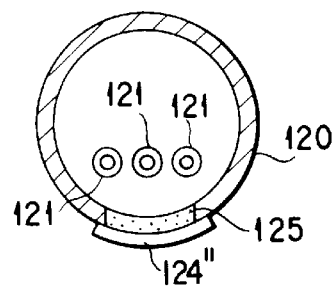

FIG. 6 shows a transmission type X-ray generator in which the positional relation between three cathodes 121 and an anode 124' is opposite to that in the reflection type of FIG. 5. FIG. 7 shows a transmission type X-ray generator in which an anode 124" is placed outside the X-ray transmitting window 125.

Figure 8:
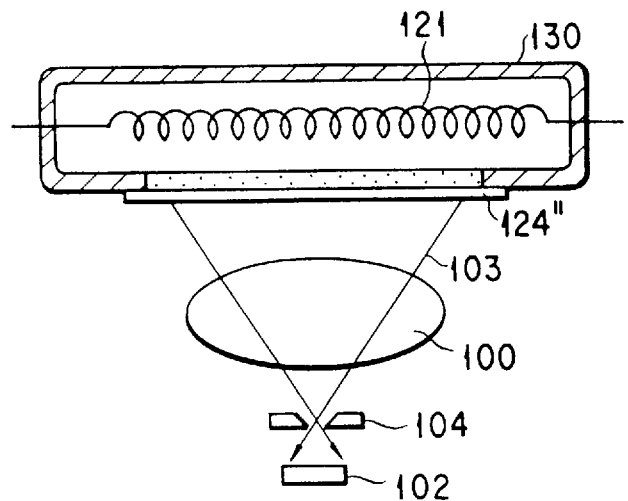
FIG. 8 shows still another embodiment of the convergence type of two-dimensional X-ray generator of the present invention.
Figure 9:
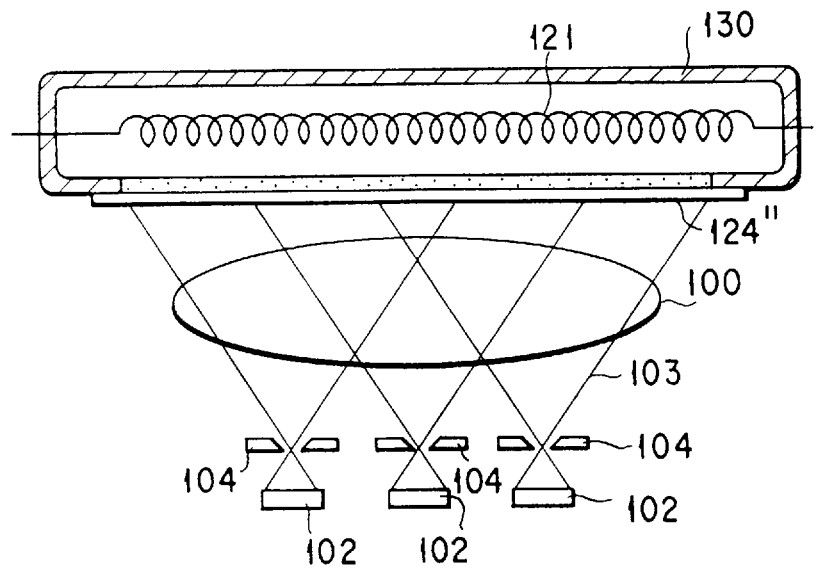
FIG. 9 shows the relationship among the convergence type of two-dimensional X-ray generator of the present invention, an X-ray sensor, and a pinhole member.

As shown in FIG. 8, a pinhole member 104 is interposed between an X-ray generator 130 which is one of the examples shown in FIGS. 4 to 7 and an X-ray sensor 102, which permits X-ray imaging of an object 100 in a large field of view regardless of a small field of view of the X-ray sensor. As shown in FIG. 9, a plurality of pinhole members 104 and an equal number of X-ray sensors 102 can be provided so that each pinhole member and the corresponding X-ray sensor are placed to face each other, providing an even larger photographing field of view. The embodiments of FIGS. 8 and 9, the dead space in the image view of field may not be produced.

Figure 10:
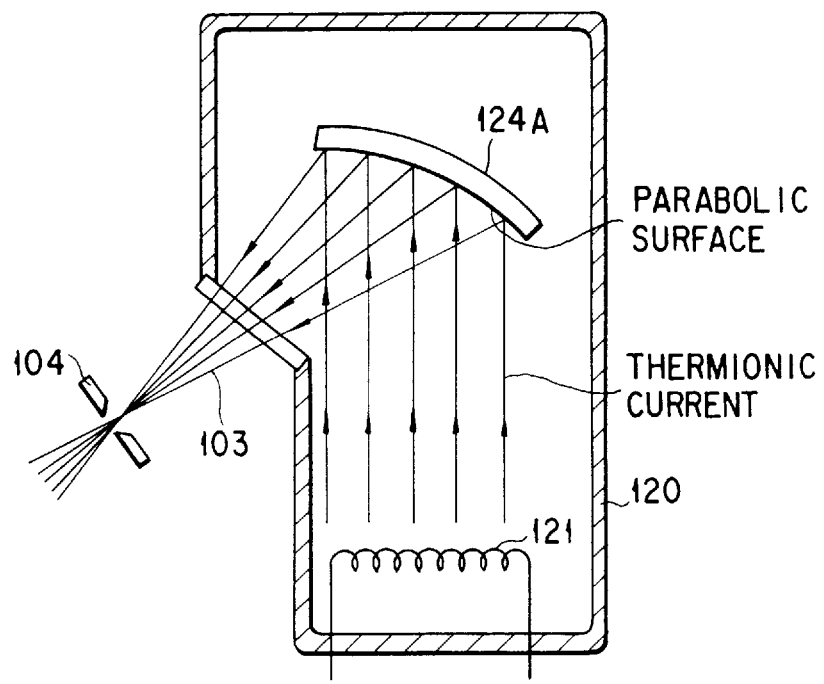
FIG. 10 shows a further embodiment of the convergence type of two-dimensional X-ray generator of the present invention.

In FIG. 10, thermoelectrons emitted from the cathode 121 in the vacuum vessel 120 are accelerated in the direction of anode to collide with an anode 124A. The collision energy is converted into X-ray energy, thereby producing X-rays. When the anode 124A has a parabolic surface with focus at the pinhole member 104, the percentage of X-rays that pass through the pinhole member 104 is large as compared with the case where the anode has another surface shape. The parabolic surface has the property of reflecting collimated light rays to converge onto its focus. It is known that the angle at which thermoelectrons collide with the anode and the angle at which most of X-rays to be generated are emitted from the anode are equivalent to the incidence angle and the reflection angle of light. Most of X-rays pass through the pinhole member as shown in FIG. 10. In practice, the parabolic surface is costly to shape by polishing; thus a curved surface is used which is easy to shape. It is natural that this curved surface should be one that is as close to paraboloid as possible. In the present invention, this is called an approximate parabolic surface. An example of an anode shaped into an approximate parabolic surface is one that is made of glass and has its surface coated with a film of tungsten formed by means of sputtering or thermal spraying. Another example is one that is made of aluminum and has its surface coated with a film of tantalum or tungsten formed by means of evaporation techniques.

In FIGS. 11A, 11B and 11C, assume that the X-ray sensor 102 travels at the same speed as the object 100. A simple X-ray image of the object 100 is produced on the X-ray sensor 102 by X-rays emitted from the X-ray generator 130 as the object and the sensor move as shown in FIGS. 11A, 11B, and 11C. The X-ray sensor 102 of FIGS. 11A, 11B and 11C is a two-dimensional sensor, which is a photographic film by way of example. In order to obtain clear X-ray images, the focus dimensions need to be small. Making the diameter of the hole in the pinhole member 104 permits clear X-ray images to be produced. The reason is that the pinhole member corresponds to the size of the focus of the X-ray tube. In FIGS. 11A, 11B and 11C, the X-ray generator 130 and the pinhole member 104 are at rest, and the object 100 and the sensor 102 move. Conversely, the X-ray generator 130 and the pinhole member 104 may move with the object 100 and the sensor 102 at rest. Or, all of them may move.

In FIGS. 11A, 11B and 11C, the X-ray sensor 102 may be a two-dimensional CCD image sensor. At the condition of the simple X-ray imaging without tomographic imaging, in order to increase the amount of X-rays incident onto the CCD sensor 200 by a predetermined amount, the pinhole member 104 may be provided with a large number of pinholes and a large number of slit plates may additionally be arranged vertically. That is, since making the diameter of the hole in the pinhole member smaller to obtain a smaller focus reduces the amount of transmitted X-rays, a multi-layer slit type pinhole member is used which consists of the pinhole member and a set of slit plates.

The relationship cross sections of the subject have with the CCD device (a two-dimensional CCD image sensor) in the X-ray sensor 102 will be described with reference to FIG. 12. The sensor 102 comprises an X-ray source (not shown), a pinhole member, and a CCD device. The subject is moved to form images of the cross sections SL1 to SL4.

Those parts of the cross sections SL1 to SL4 which have the same area are viewed from the pinhole of the pinhole member. The view angle R' with respect to the lowermost section SL4 is larger than those with respect to the sections SL1 to SL3. The view angle R with respect to the uppermost section SL1 is smaller than those with respect to the other sections SL2 to SL4. The images of the sections SL1 to SL4 are projected through the pinhole onto the light-receiving surface of the CCD device. Of these images, the image of the lowermost section SL4 moves most fast and the image of the uppermost section SL1 moves most slowly.

The CCD device is moved from point q to point p while the uppermost section SL1 is being moved from point P to point Q, thereby successfully forming an image of the cross section SL1 of the subject. Similarly, the CCD device is moved while the second uppermost section SL2 is moved for the same distance between the points P and Q, thereby forming an image of the cross section SL2 of the subject. Further, the CCD device is moved while the third uppermost section SL3 is being moved for the same distance between points P and Q, forming an image of the cross section SL1 of the subject. The CCD device is moved from point q' to point p' while the uppermost section SL1 is being moved from point P' to point Q', thereby forming an image of the cross section SL1 of the subject.

The present embodiment has a single CCD device, which is moved at different speeds to form the images of different cross sections of the subject, one after another. According to the invention, the X-ray sensor 102 may have a plurality of CCD devices, which are simultaneously moved at different speeds to form the images of different cross sections of a subject, at the same time. Various methods of forming the images of different cross sections of a subject, according to the invention, will be described later, with reference to FIGS. 31, 33 and 35.

Reference will now be made to FIGS. 13A, 13B and 13C to describe a method of driving the two-dimensional CCD image sensor 200. In this driving method, a charge produced in each M×N pixel of the CCD is moved in the VD direction (vertical driving direction or "N" direction of the FIGS. 13A, 13B and 13C) and it is stored and added in the VD direction, as shown in FIGS. 13A, 13B and 13C. In this specification, the two-dimensional CCD to which this driving method is applied is referred to as a moving storage type CCD 300, which is the abbreviated form of the stored charge moving addition type CCD.

Although, in FIGS. 11A, 11B, 11C and FIG. 14, the two-dimensional CCD image sensor 200 is moved at the same speed as the object, the moving storage CCD may be at rest as shown in FIG. 15. This is because stored charges move in place of the CCD.

Owing to the provision of the pinhole member 104, the imaging method and apparatus of the present invention are not affected by scattered rays. That is, the scattered rays are eliminated by the pinhole member. Small focus dimensions can be achieved by making small the diameter of the hole in the pinhole member 104. When the diameter of the hole in the pinhole member is made small, the quantity of X-rays incident on the X-ray sensor reduces, which may require a high-sensitivity X-ray sensor to obtain X-ray images. In such a case, the moving storage CCD is used that is highly sensitive. The combination of an image intensifier that has a double-sensitivity device with a CCD will provide a much higher sensitivity. In other words, the diameter of the hole in the pinhole member can be made much smaller.

In the direct tomography, the clearness of images can be improved by making the angle ANG shown in FIG. 2A large. When, as shown in FIG. 16, a plurality of X-ray generators 101 are arranged in an arc, it becomes possible to make large the effective convergence and divergence angles (corresponding to the angle ANG) associated with the pinhole member 104. According to an experiment, good tomographic images were obtained by setting the angle to 50 degrees or more.

Figure 20:
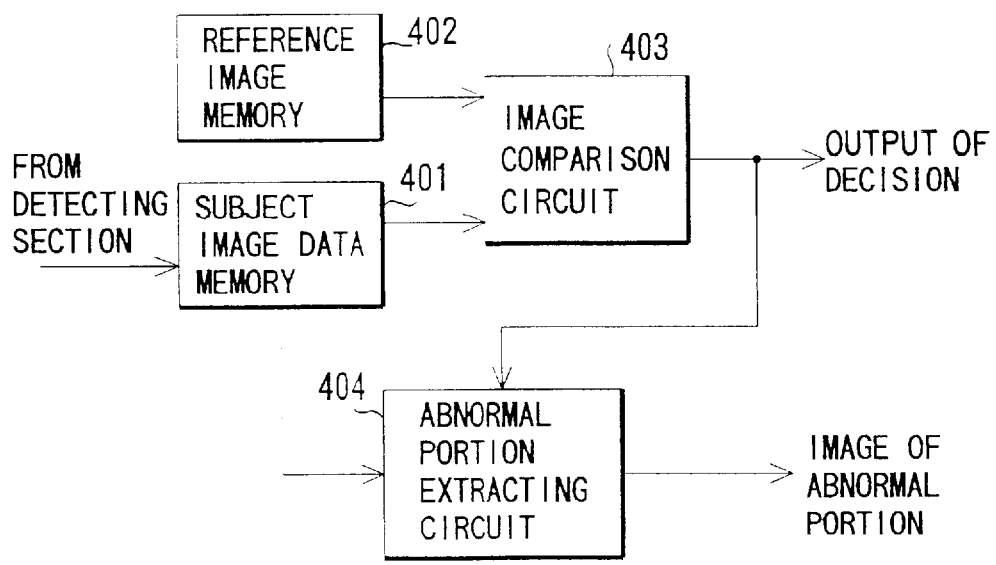
FIG. 20 is a block diagram of a signal processing system of the present invention.

In FIG. 17 there is illustrated the state where slices (plane sections) SL1 to SL5 are imaged simultaneously. Five pinhole members $104_1$ to $104_5$ and five storage type X-ray sensors $300_1$ to $300_5$ are placed so that the corresponding pinhole member and X-ray sensor face each other, thereby making the equivalent travel speed of each of the X-ray sensors equal to the equivalent travel speed of a corresponding one of the slices of the object 100. For example, the equivalent travel speed of the sensor $300_1$ becomes equal to the equivalent travel speed of the slice SL1 and the succession on the assembly line. An example of such a product is a die-casting product, which often needs tomography-based inspection for its defects (e.g., casting cavities). In the present invention, unlike computerized tomography (CT), no calculation time is required to produce tomographic images; hence, sectional images of an object can be obtained in real time. It therefore becomes possible to make real-time tomography-based inspection of products that, like running sheets, are carried continuously or products that, like die-casting products, are carried serially. In the tomography-based inspection, a normal sectional image of a normal product is referenced for comparison with a sectional image of a product to be inspected. A signal processing system which, as shown in FIG. 20, comprises an object image memory 401 which receives and stores image data from the sensor, a reference image memory 402, an image comparator 403, and an abnormal portion extractor 404 can be used to make a normal/abnormal decision for each product.

For some objects, attention must be paid so that they will not be exposed to unwanted X-rays. A human body is an example of such an object. In order to minimize radiation damage, it is required to minimize unwanted X-ray exposure.

In FIG. 21, of radiation emitted from a two- or three-dimensional radiation source 101, necessary rays equivalent travel speed of the sensor 300$_2$ becomes equal to the equivalent travel speed of the slice SL2. By so doing, the slices SL1 to SL5 can be imaged simultaneously.

FIG. 18 shows the case where the storage type X-ray sensor is the moving storage CCD 300. In this case, a combination of a pinhole member 104 and a moving storage CCD 300 is used. In FIG. 18, the equivalent moving speed of stored carriers for slices SLA, SLB and SLC becomes slow in the order of SLA, SLB, and SLC. For example, by making the equivalent moving speed of stored charges equal to the moving speed of the slice SLB, the image of the slice SLB can be obtained. In order to obtain images of multiple slices at the same time, it is required to move the object 100 at high speed or move the pinhole member 104 and the X-ray sensor 200 (300) together at high speed.

Figure 19:
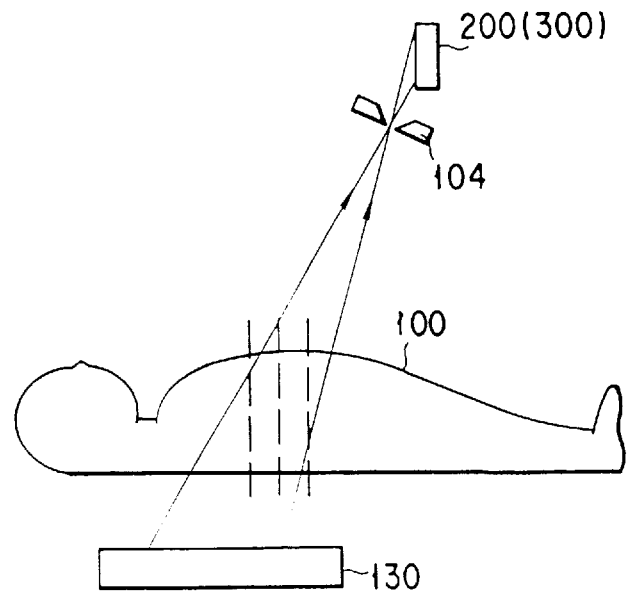
FIG. 19 shows a method of obtaining a tomographic image in accordance with the present invention.

In FIG. 19, when the object 100 is stationary, the storage type X-ray sensor 200 may be moved either in an up-and-down direction on the drawing paper (parallel to the drawing paper) or perpendicular to the drawing paper. When the object is moving, on the other hand, the X-ray sensor 102 may be stationary provided that it is the moving storage CCD 300.

The object in the present invention will be described. In many cases, a lot of industrial products identical in shape are produced and carried in 103A, which are indicated by solid lines, pass through the object 100 and the pinhole member 104 and reach the storage type image sensor 200, thereby producing a tomographic image (sectional image). On the other hand, unnecessary rays 103B are indicated by dotted lines, which are not useful in making the tomography image.

In FIG. 22, an X-ray alignment member 500 is placed between the two- or three-dimensional X-ray source 101 and the object 100, which allows the necessary radiation 103A to pass through the pinhole member 104 and reach the storage type image sensor 200 and blocks the unnecessary X-rays 103B.

FIG. 23 is a plan view of the X-ray alignment member 500. A large number of holes 500A are formed in the member 500. FIG. 24 is a sectional view taken along line XXIV—XXIV of FIG. 23. The member 500 consists of an upper alignment plate 500$_1$ and a lower alignment plate 500$_2$. The holes in the upper and lower alignment members are positioned so that X-rays 103 will pass through the pinhole member 104 and reach the storage type image sensor 200. Each of the upper and lower alignment plates can be individually formed with holes and, in forming the holes, can be processed perpendicular to it because it is small in thickness. This facilitates hole processing. When, as shown in FIG. 22, the alignment member 500 consists of a single plate as shown in FIG. 22, the plate must be processed diagonally to form holes and the inclination varies from hole to hole. This makes the manufacture of the member difficult. Though shown as circular in FIG. 23, the hole can take any other shape, such as square, hexagon, or the like. For this purpose, it is preferable that the X-ray alignment member be a thin plate.

FIG. 25 schematically shows a positional relation between the holes in the X-ray alignment member and the pinhole member. If the holes in each of the upper and lower alignment plates 500$_1$ and 500$_2$ are formed an equal pitch, and the coordinates of the centers of the corresponding holes in the upper and lower plates have a proportional relationship (i.e., proportional enlargement or reduction), then X-rays 103 passed through the two alignment plates will converge onto a single point. This can be proved geometrically as shown in FIGS. 26 and 27.

FIG. 26 is a schematic illustration of a part of FIG. 25. First, let C be the point at which radiation AB and DE intersect. Let us prove that the extension of EG passes through C in FIG. 25. ADF and BEG are parallel to each other, and AD=DF and BE=EG. Let G' be the point at which the line connecting F and C intersects the lower alignment plate 500$_2$. Then, it is required to prove that G' coincides with G. The triangle CDF and the triangle CEG' are similar to each other. Thus, since AD=DF, BE=EG'. From the equal pitch assumption, BE=EG. Thus, EG=BE=EG'. It was thus proved that G' coincides with G.

Although FIG. 25 is shown one-dimensionally, the above proof likewise holds for two dimensions. In practice, the upper and lower alignment plates are two-dimensional. A large number of beams of X-rays that converge onto a single point are distributed two-dimensionally.

Figure 28:
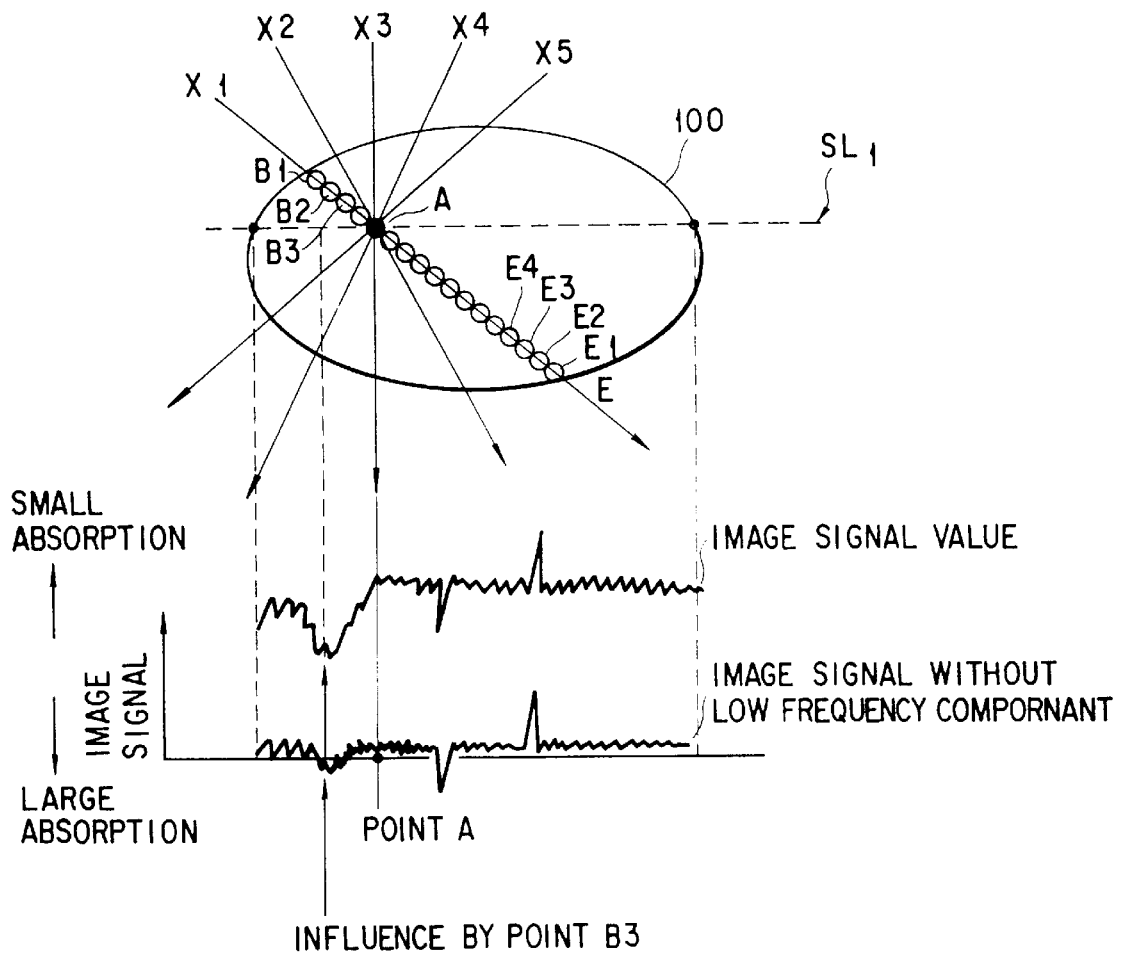
FIG. 28 is a diagram for use in explanation of the function of a highpass filter.

FIG. 28 is an enlarged view of part of FIGS. 2A to 2C. In FIG. 28, a beam of X-rays X1 passes through the object and reaches the storage type image sensor while undergoing absorption at points B1, B2, B3, . . . , A, . . . , E4, E3, E2, E1. Assuming that, in this process, very strong absorption occurs at point B3, a tomographic image value in the vicinity of the B3 point in a specific slice S11 of the object 100 will be affected. In FIG. 28 there is illustrated the effect of the point B3 on signal values with coordinate positions in the direction of travel of the object as the axis of abscissa and image signal values as the axis of ordinate. When the absorption is small, the signal value becomes large and vice versa. Even an image signal value at point A at which beams of X-rays X1, X2, X3, X4, X5, . . . , XN (N is a large number) pass through may be affected by the absorption at point B3.

The point B3 have an effect on all portions in the vicinity of B3. The reason is that X-rays passing through B3 exist over the range of at least 50 degrees or more. Thus, the effect of B3 appears as low frequency components (not sufficiently averaged) in an electronic waveform. When a highpass filtering process is performed on the waveform, a signal waveform as expressed in FIG. 28 as an image signal having low frequency components removed results. Thus, the effect of point B3 is minimized.

As an example, when the object is a human body and tomographic images are observed to identify the diseased part and judge the conditions of that part, it is often desired that the tomographic images look stereoscopic. In imaging diagnosis of a specific internal organ, it is preferable that images before and behind that organ look lightly superimposed upon each other to provide stereoscopic vision. This will make it easy to judge the relationship between the organ and the surrounding region, providing good visibility.

On the other hand, the CT is, in principle, adapted to produce only an image of a plane section of a body and thus provides no information in the direction of depth. In order to produce a stereoscopic image, therefore, it must be produced from a plurality of images for plane sections of the body, requiring lengthy calculations. In addition, it is difficult to produce a complete stereoscopic image because of spacing between each plane section.

In principle the CT has the possibility that image artifacts may be produced. In the present invention, on the other hand, there is no requirement of making calculations to produce an image of a plane section because of direct tomography and image artifacts will not be produced intrinsically.

Figure 29:
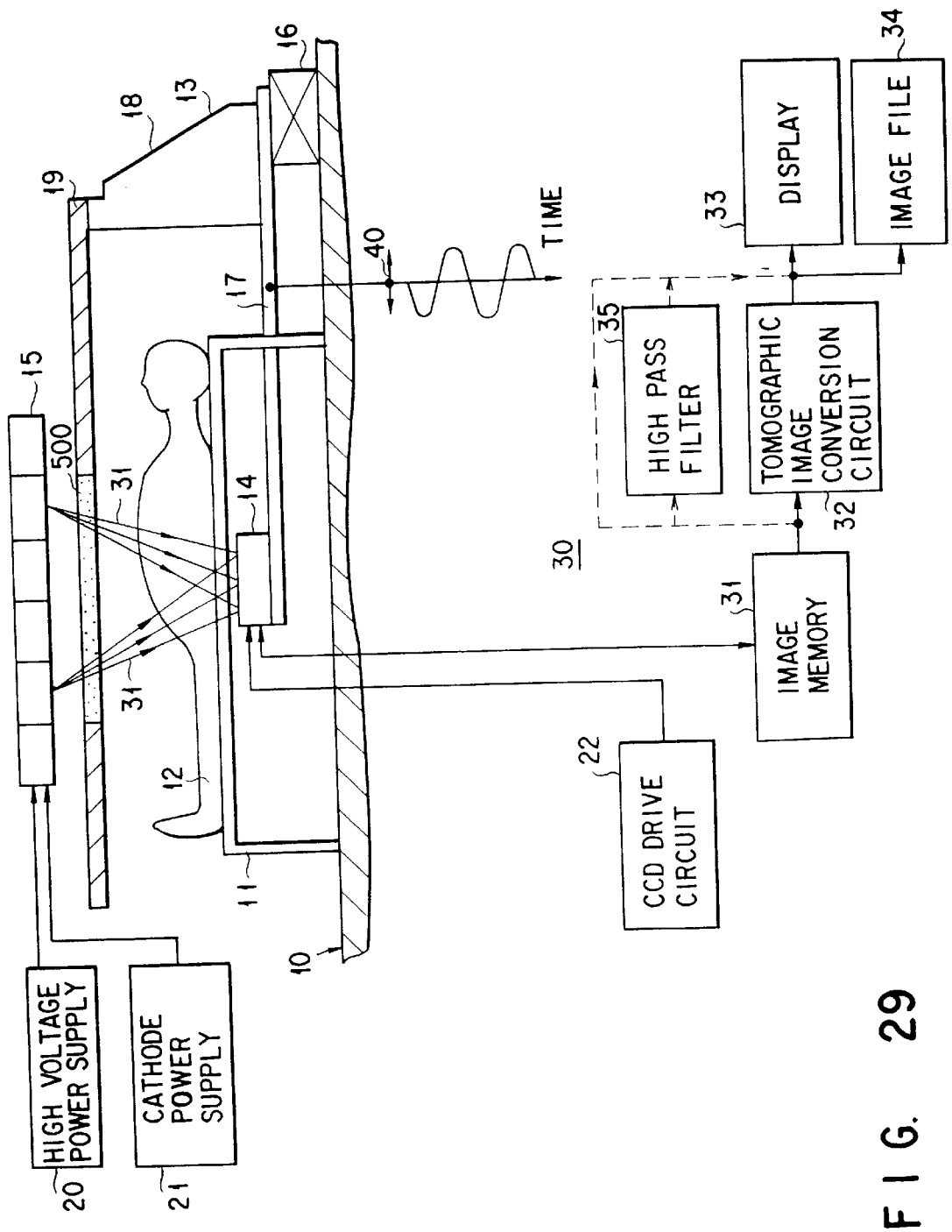
FIG. 29 shows a living body tomographic apparatus of the present invention.

Hereinafter, the embodiments of the present invention will be described with reference to the drawings. FIG. 29 shows an embodiment of the present invention that is directed to medical applications. As shown in FIG. 29, a couch 11 is placed on floor 10. A human body 12 under examination is laid down on the couch 11. An X-ray sensor unit 14 supported by a frame apparatus 13 is placed below the couch 11 and an X-ray source 15 supported by a support member not shown is placed above the couch. The frame apparatus 13 is equipped with a frame driving unit 16 mounted on the floor, a member 17 coupled with the frame driving unit 16 for mounting the X-ray sensor unit 14, a frame 18, and an X-ray shield member 19 having an X-ray alignment member 500 having apertures formed at an equal pitch. The frame drive unit 16 repeatedly moves the member 17, the frame 18, and the X-ray shield member 19 together in the directions indicated at 40. To the X-ray source 15 are connected a high-tension power source 20 and a cathode power source 21 for providing to the X-ray source predetermined anode and cathode voltages required for the X-ray source to produce X-rays 31.

In the present embodiment, the radiation source 15 that is two- or three-dimensional comprises a number of X-ray tubes which are juxtaposed as shown. The juxtaposition of the X-ray tubes is intended to make the total angle of radiation large. Part of X-rays 31 are blocked by the X-ray shield member 19 and the X-ray alignment member 500 and the remaining X-rays pass through the X-ray alignment member and the human body 12 and enter the X-ray sensor unit 14.

The X-ray sensor unit 14 comprises, as its major component, a CCD which is driven by a CCD driver 22. An output signal of the X-ray sensor unit 14 is applied to a signal processing unit 30, which comprises an image memory 31, a tomographic image converter 32, a display unit 33, an image file 34, and a highpass filter 35. The highpass filter is connected in parallel with the tomographic image converter 32 between the image memory 31 and the display unit 33 as needed. The image memory 31 and the display unit 33 may be connected directly as needed.

Figure 30:
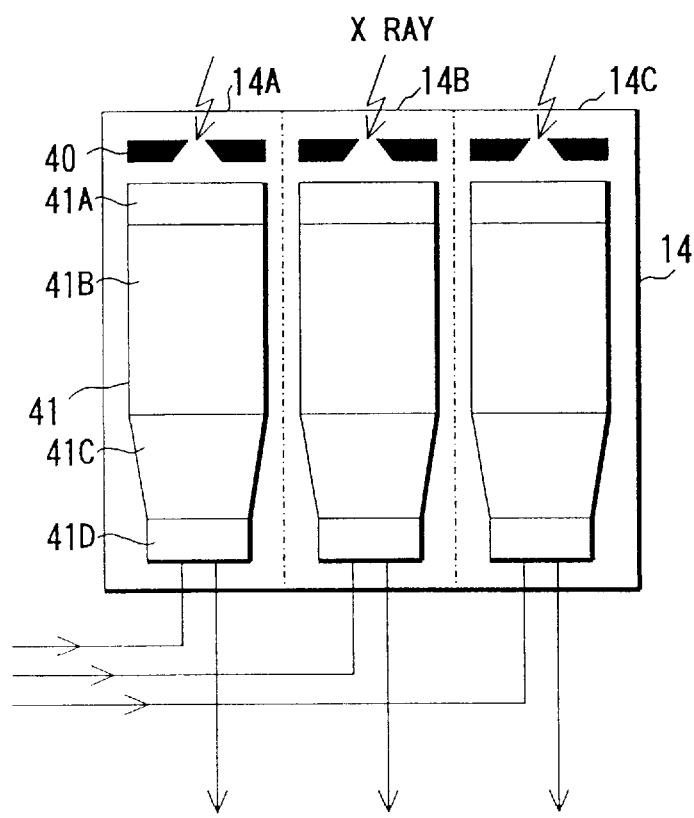
FIG. 30 shows the structure of the X-ray sensor unit of FIG. 29.

The X-ray sensor unit 14 comprises three X-ray sensor elements 14A, 14B, 14C as shown in FIG. 30, each of which having a pinhole member 40 (spatial filter) and a sensor 41. The sensor consists of a scintillator 41A, an image intensifier 41B, an optical system 41C, and a two-dimensional CCD image sensor 41D that is a storage type image sensor.

The object 12 is stationary and the shield member, the X-ray alignment plate 500 and the sensor 41 including the spatial filter 40 are fixed to the frame 18. The frame 18 is reciprocated as shown in FIG. 29 by the frame drive unit 16. In FIG. 10, three storage type image sensors are arranged in a line. Assume that three lines each of three sensors are arranged perpendicular to the direction of movement of the frame. Then, images of 18 (=3×3×2) plane sections will be obtained at each reciprocation of the frame. Assuming that the frame makes 10 reciprocations a second, 180 (=3×3×2× 10) images will be obtained in one second.

The CCD image sensor 41D is supplied with drive signals from the CCD driver 22 so that the speed of movement of stored charges in it is made equivalently equal to the speed of movement of each plane section of the object. Output signals of the CCD image sensor are stored in the image memory 31. When there is no need of conversion of angles of plane sections, the image signal is transferred to the display unit 33 and the image file 34 for image display and recording without being applied to the sectional image converter 32. When there is need for an image of a plane section that is not parallel to (or has some angle with respect to) the direction of equivalent movement of the object, the image is converted to one of a desired angle in the image converter 32 and then transferred to the display unit 33 and the image file 34. In this case, the image conversion circuit 32 may include the highpass filter 35 when necessary.

Figure 31:
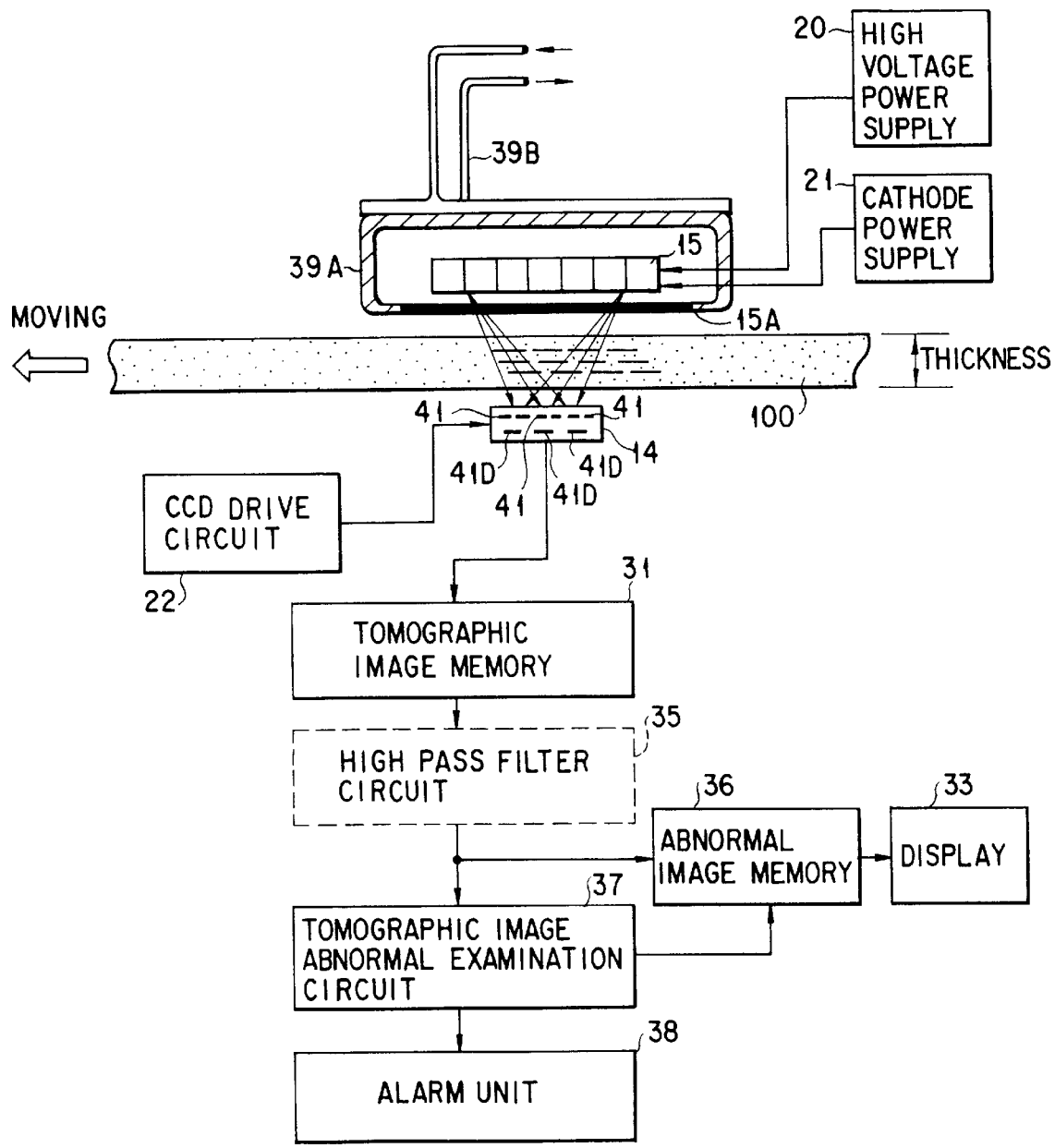
FIG. 31 shows a steal slab defect inspection system of the present invention.

Other embodiments of the present invention will be described with reference to FIGS. 31 to 35. In FIG. 31, the object 100 is a steel slab which is produced by a continuous casting machine and is in a high-temperature red heat state. The object moves in the direction indicated by an arrow. The object has a shape as shown in FIG. 32 and typically is about 150 millimeters in thickness, about 1 to 3 meters in width, and about 100 meters in length. The object moves at a speed of about 0.1 meters per second in the direction of the arrow. The section of the slab is rectangular as shown in FIG. 32.

The main purpose of the tomography of steel slab is to inspect defects of products. Defects include contamination by foreign materials, surface cracks, cracks in the vicinity of surface, voids in the vicinity of surface, etc. Among these defects, the noticeable one is cracks in the vicinity of surface. Such cracks are harmful and likely to remain or spread in the subsequent rolling process. Cracks existing inside are squeezed in the subsequent rolling process, so that they become harmless. On the other hand, foreign materials are harmful regardless of where they are.

As described above, the general inspection for steel slab over its entire thickness is not sufficient for its in-line inspection and the inspection by plane section in the direction of thickness is required. To this end, images of plane sections are required.

In FIG. 31, the high tension power source 20 supplies a high voltage to the X-ray tubes 15 that are arranged two- or three-dimensionally. The cathode of each X-ray tube is heated by power from the cathode power-source 21. In order to protect the X-ray tubes 15 from ambient high-temperature atmosphere, they are housed in an X-ray tube container 39A and cooled by water supplied through water cooling pipes 39B. On the X-ray emitting side of the container is placed a heat reflecting plate 15A that is plated with nickel of good reflectance to reflect heat rays from the read-heated slab.

X-rays emitted from the X-ray tube 15 pass through the steel slab which is an object and enters the X-ray sensor unit 14 as shown in FIG. 30. In the X-ray sensor unit, the X-rays pass through the pinhole 40 and enter the corresponding CCD image sensor 41D. The number of image sensors is at least three in the direction of movement of the object 100 and from several to hundred in the direction of width, depending on the width measurement. Since at least three image sensors are arranged in the direction of movement of the object, at least three plane sections of the object, such as its upper, central and lower surface layers, can be imaged.

Signals from imaging plane sections are processed as shown in FIG. 34. In FIG. 34, the axis of ordinates shows the CCD output and the axis of abscissas is taken in the direction of width. In the presence of a crack, the X-ray transmission increases at its site, increasing the magnitude of a signal. It is compared with a predetermined inspection level to make a decision whether it is a defect or not. An output signal of the CCD image sensor 41D is processed by the image memory 31, the highpass filter 35, and an abnormal image check circuit 37. The result of the decision is output to an alarm device 38. An abnormal image is stored in an image memory 36 and output to the display unit 33. As with the X-ray tubes, the CCD image sensor 41D is housed in a water cooled container for heat insulation.

In FIG. 31, there is illustrated an arrangement to inspect three plane sections of the object. In order to increase the number of plane sections to be inspected, the number of image sensors may be increased in the direction of movement of the object or a plurality of blocks each of which has such an arrangement as shown in FIG. 31 may be arranged in the direction of movement of the object.

Figure 35:
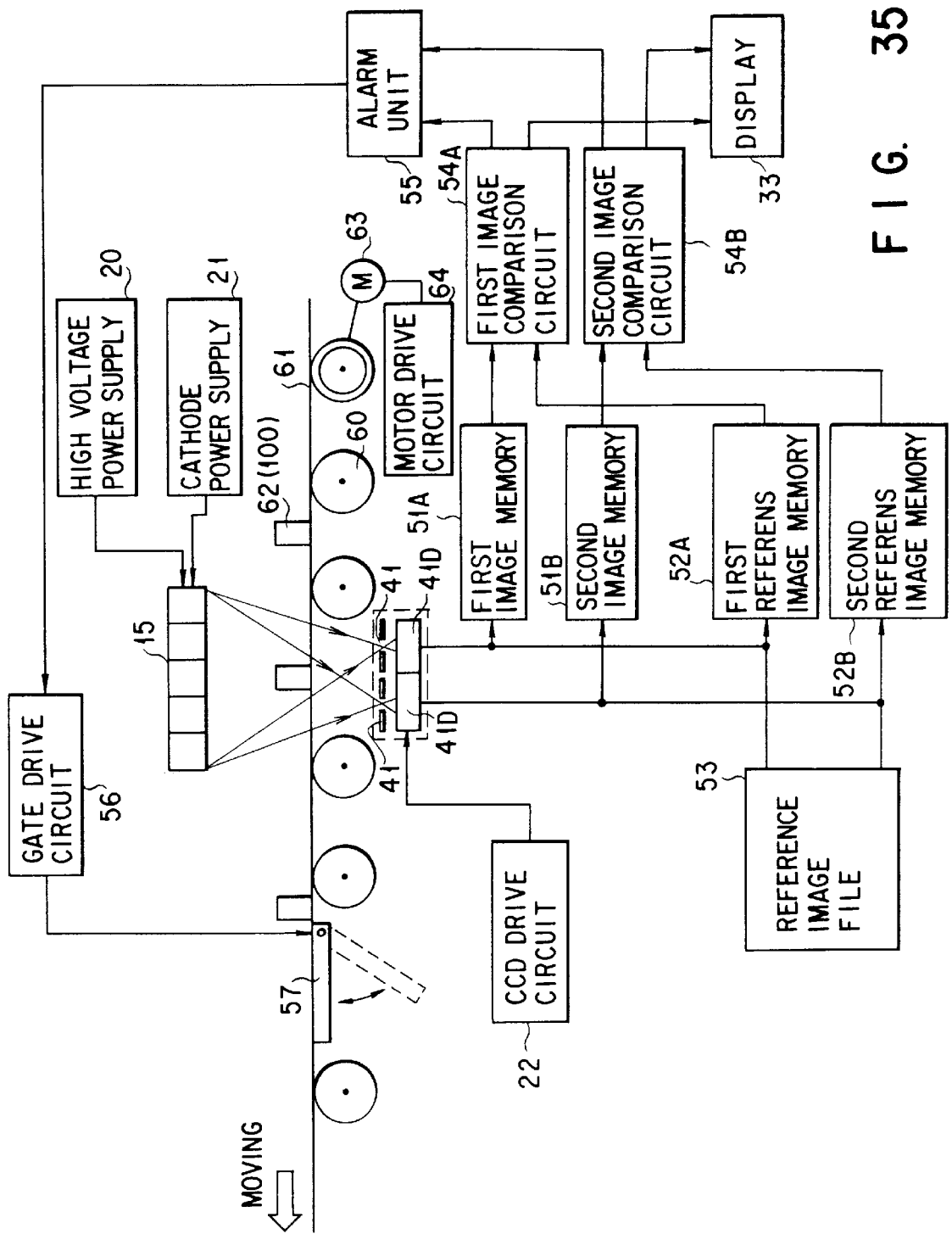
FIG. 35 shows a die-casting defect inspection system of the present invention.

Still another embodiment of the present invention will be described with reference to FIG. 35. In FIG. 35, the object is a die-castings 62. The die-castings are manufactured by the identical metallic mold; thus, they are identical in dimensions and shape. In the die-castings, however, defects such as voids may be produced and dimensional abnormalities due to chips or the like may occur. For this reason, inspection is essential for quality control. However, depending on where they are, the voids or chips may not become the problem in quality and function. It is therefore desirable to make inspection for planar section. As shown in FIG. 35, the objects 100 are carried one after another on a conveyer belt 61. The belt is moved by rollers 60, which are driven by motor 63 driven by a motor driver 64.

In FIG. 35, two CCD image sensors 41D are arranged for inspection of two plane sections. Output signals of the CCD image sensors 41D are stored in image memories 51A and 51B and then compared with signals supplied through reference image memories 52A and 52B from a reference image file 53 for the good object in image comparators 54A and 54B. As the result of the comparison, an image of the object that was determined to be defective is displayed on the display 33 and an alarm device 55 issues a defect indicating signal to a gate driver 56. In response to that abnormality indicating signal, the gate driver opens a gate 57 to remove the defective object.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

I claim:

1. An X-ray imaging system for an object comprising:

a convergence type X-ray generating unit for producing X-rays having an X-ray bundle so that it converges onto a given location;

an X-ray sensor unit opposed to the X-ray generating unit with the object interposed therebetween;

a pinhole member placed between the object and the X-ray sensor unit; and a signal processing unit for processing an output signal of the X-ray sensor unit.

2. The system according to claim 1, further comprising means for moving the X-ray generating unit, the pinhole member, and the X-ray sensor unit relative to the object.

3. The system according to claim 1, wherein the X-ray sensor unit includes a storage type two-dimensional X-ray sensor which has means for moving storage charges at a speed corresponding to the relative speed of movement of the object and the X-ray sensor unit.

4. The system according to claim 1, wherein the convergence type X-ray generating unit comprises a plurality of convergence type X-ray generators that are arranged in parallel.

5. The system according to claim 4, wherein the X-ray sensor unit includes a moving and storing type CCD arranged each that stored charges are moved and added, and means for moving storage charges in the moving and storing type CCD at a speed corresponding to the relative speed of movement of a specific plane section within the object and the moving and storing type CCD.

6. The system according to claim 1, wherein the signal processing system includes a highpass filter.

7. The system according to claim 1, wherein the pinhole member has a hole the diameter of which is set such that the convergence and divergence angles of radiation become 50 degrees or more.

8. The system according to claim 1, wherein the pinhole member and the X-ray sensor unit are placed close to each other.

9. The system according to claim 1, wherein the pinhole member comprises a pinhole plate and a slit plate.

10. The system according to claim 1, further comprising an alignment member interposed between the X-ray generating unit and the object for suppressing exposure of the object to radiation that does not fall on the X-ray sensor unit.

11. The system according to claim 10, wherein the alignment member includes first and second alignment plates which are arranged in parallel and have a large number of holes, the coordinates of the center of each hole in the second alignment plate being proportionally reduced or enlarged with respect to those of the corresponding hole in the first alignment plate.

12. A method of X-ray imaging an object comprising the steps of:

producing X-rays having X-ray bundle so that it converges onto a predetermined point;

irradiating the object with the X-rays;

sensing X-rays passed through the object through a pinhole member; and processing an X-ray detect signal.

* * * * *

UNITED STATES PATENT AND TRADEMARK OFFICE
CERTIFICATE OF CORRECTION

PATENT NO. : 5,805, 663
DATED : Sep. 8, 1998
INVENTOR(S) : Mihara

It is certified that error appears in the above-identified patent and that said Letters Patent is hereby corrected as shown below:

Please delete columns 7,8,9,10 and substitute columns 7,8,9 and 10 as per attached.

Signed and Sealed this

Thirteenth Day of March, 2001

Attest:

NICHOLAS P. GODICI

*Attesting Officer*  *Acting Director of the United States Patent and Trademark Office*

X-ray image of the object 100 is produced on the X-ray sensor 102 by X-rays emitted from the X-ray generator 130 as the object and the sensor move as shown in FIGS. 11A, 11B, and 11C. The X-ray sensor 102 of FIGS. 11A, 11B and 11C is a two-dimensional sensor, which is a photographic film by way of example. In order to obtain clear X-ray images, the focus dimensions need to be small. Making the diameter of the hole in the pinhole member 104 permits clear X-ray images to be produced. The reason is that the pinhole member corresponds to the size of the focus of the X-ray tube. In FIGS. 11A, 11B and 11C, the X-ray generator 130 and the pinhole member 104 are at rest, and the object 100 and the sensor 102 move. Conversely, the X-ray generator 130 and the pinhole member 104 may move with the object 100 and the sensor 102 at rest. Or, all of them may move.

In FIGS. 11A, 11B and 11C, the X-ray sensor 102 may be a two-dimensional CCD image sensor. At the condition of the simple X-ray imaging without tomographic imaging, in order to increase the amount of X-rays incident onto the CCD sensor 200 by a predetermined amount, the pinhole member 104 may be provided with a large number of pinholes and a large number of slit plates may additionally be arranged vertically. That is, since making the diameter of the hole in the pinhole member smaller to obtain a smaller focus reduces the amount of transmitted X-rays, a multilayer slit type pinhole member is used which consists of the pinhole member and a set of slit plates.

The relationship cross sections of the subject have with the CCD device (a two-dimensional CCD image sensor) in the X-ray sensor 102 will be described with reference to FIG. 12. The sensor 102 comprises an X-ray source (not shown), a pinhole member, and a CCD device. The subject is moved to form images of the cross sections SL1 to SL4.

Those parts of the cross sections SL1 to SL4 which have the same area are viewed from the pinhole of the pinhole member. The view angle R' with respect to the lowermost section SL4 is larger than those with respect to the sections SL1 to SL3. The view angle R with respect to the uppermost section SL1 is smaller than those with respect to the other sections SL2 to SL4. The images of the sections SL1 to SL4 are projected through the pinhole onto the light-receiving surface of the CCD device. Of these images, the image of the lowermost section SL4 moves most fast and the image of the uppermost section SL1 moves most slowly.

The CCD device is moved from point q to point p while the uppermost section SL1 is being moved from point P to point Q, thereby successfully forming an image of the cross section SL1 of the subject. Similarly, the CCD device is moved while the second uppermost section SL2 is moved for the same distance between the points P and Q, thereby forming an image of the cross section SL2 of the subject. Further, the CCD device is moved while the third uppermost section SL3 is being moved for the same distance between points P and Q, forming an image of the cross section SL1 of the subject. The CCD device is moved from point q' to point p' while the uppermost section SL1 is being moved from point P' to point Q', thereby forming an image of the cross section SL1 of the subject.

The present embodiment has a single CCD device, which is moved at different speeds to form the images of different cross sections of the subject, one after another. According to the invention, the X-ray sensor 102 may have a plurality of CCD devices, which are simultaneously moved at different speeds to form the images of different cross sections of a subject, at the same time. Various methods of forming the images of different cross sections of a subject, according to the invention, will be described later, with reference to FIGS. 31, 33 and 35.

Reference will now be made to FIGS. 13A, 13B and 13C to describe a method of driving the two-dimensional CCD image sensor 200. In this driving method, a charge produced in each M×N pixel of the CCD is moved in the VD direction (vertical driving direction or "N" direction of the FIGS. 13A, 13B and 13C) and it is stored and added in the VD direction, as shown in FIGS. 13A, 13B and 13C. In this specification, the two-dimensional CCD to which this driving method is applied is referred to as a moving storage type CCD 300, which is the abbreviated form of the stored charge moving addition type CCD.

Although, in FIGS. 11A, 11B, 11C and FIG. 14, the two-dimensional CCD image sensor 200 is moved at the same speed as the object, the moving storage CCD may be at rest as shown in FIG. 15. This is because stored charges move in place of the CCD.

Owing to the provision of the pinhole member 104, the imaging method and apparatus of the present invention are not affected by scattered rays. That is, the scattered rays are eliminated by the pinhole member. Small focus dimensions can be achieved by making small the diameter of the hole in the pinhole member 104. When the diameter of the hole in the pinhole member is made small, the quantity of X-rays incident on the X-ray sensor reduces, which may require a high-sensitivity X-ray sensor to obtain X-ray images. In such a case, the moving storage CCD is used that is highly sensitive. The combination of an image intensifier that has a double-sensitivity device with a CCD will provide a much higher sensitivity. In other words, the diameter of the hole in the pinhole member can be made much smaller.

In the direct tomography, the clearness of images can be improved by making the angle ANG shown in FIG. 2A large. When, as shown in FIG. 16, a plurality of X-ray generators 101 are arranged in an arc, it becomes possible to make large the effective convergence and divergence angles (corresponding to the angle ANG) associated with the pinhole member 104. According to an experiment, good tomographic images were obtained by setting the angle to 50 degrees or more.

In FIG. 17 there is illustrated the state where slices (plane sections) SL1 to SL5 are imaged simultaneously. Five pinhole members $104_1$ to $104_5$ and five storage type X-ray sensors $300_1$ to $300_5$ are placed so that the corresponding pinhole member and X-ray sensor face each other, thereby making the equivalent travel speed of each of the X-ray sensors equal to the equivalent travel speed of a corresponding one of the slices of the object 100. For example, the equivalent travel speed of the sensor $300_1$ becomes equal to the equivalent travel speed of the slice SL1 and the equivalent travel speed of the sensor $300_2$ becomes equal to the equivalent travel speed of the slice SL2. By so doing, the slices SL1 to SL5 can be imaged simultaneously.

FIG. 18 shows the case where the storage type X-ray sensor is the moving storage CCD 300. In this case, a combination of a pinhole member 104 and a moving storage CCD 300 is used. In FIG. 18, the equivalent moving speed of stored carriers for slices SLA, SLB and SLC becomes slow in the order of SLA, SLB, and SLC. For example, by making the equivalent moving speed of stored charges equal to the moving speed of the slice SLB, the image of the slice SLB can be obtained. In order to obtain images of multiple slices at the same time, it is required to move the object 100 at high speed or move the pinhole member 104 and the X-ray sensor 200 (300) together at high speed.

In FIG. 19, when the object 100 is stationary, the storage type X-ray sensor 200 may be moved either in an up-and-down direction on the drawing paper (parallel to the drawing paper) or perpendicular to the drawing paper. When the object is moving, on the other hand, the X-ray sensor 102 may be stationary provided that it is the moving storage CCD 300.

The object in the present invention will be described. In many cases, a lot of industrial products identical in shape are produced and carried in succession on the assembly line. An example of such a product is a die-casting product, which often needs tomography-based inspection for its defects (e.g., casting cavities). In the present invention, unlike computerized tomography (CT), no calculation time is required to product tomographic images; hence, sectional images of an object can be obtained in real time. It therefore becomes possible to make real-time tomography-based inspection of products that, like running sheets, are carried continuously or products that, like die-casting products, are carried serially. In the tomography-based inspection, a normal sectional image of a normal product is referenced for comparison with a sectional image of a product to be inspected. A signal processing system which, as shown in FIG. 20, comprises an object image memory 401 which receives and stores image data from the sensor, a reference image memory 402, an image comparator 403, and an abnormal portion extractor 404 can be used to make a normal/abnormal decision for each product.

For some objects, attention must be paid so that they will not be exposed to unwanted X-rays. A human body is an example of such an object. In order to minimize radiation damage, it is required to minimize unwanted X-ray exposure.

In FIG. 21, of radiation emitted from a two- or three-dimensional radiation source 101, necessary rays 103A, which are indicated by solid lines, pass through the object 100 and the pinhole member 104 and reach the storage type image sensor 200, thereby producing a tomographic image (sectional image). On the other hand, unnecessary rays 103B are indicated by dotted lines, which are not useful in making the tomography image.

In FIG. 22, an X-ray alignment member 500 is placed between the two- or three-dimensional X-ray source 101 and the object 100, which allows the necessary radiation 103A to pass through the pinhole member 104 and reach the storage type image sensor 200 and blocks the unnecessary X-rays 103B.

FIG. 23 is a plan view of the X-ray alignment member 500. A large number of holes 500A are formed in the member 500. FIG. 24 is a sectional view taken along line XXIV—XXIV of FIG. 23. The member 500 consists of an upper alignment plate $500_1$ and a lower alignment plate $500_2$. The holes in the upper and lower alignment members are positioned so that X-rays 103 will pass through the pinhole member 104 and reach the storage type image sensor 200. Each of the upper and lower alignment plates can be individually formed with holes and, in forming the holes, can be processed perpendicular to it because it is small in thickness. This facilitates hole processing. When, as shown in FIG. 22, the alignment member 500 consists of a single plate as shown in FIG. 22, the plate must be processed diagonally to form holes and the inclination varies from hole to hole. This makes the manufacture of the member difficult. Though shown as circular in FIG. 23, the hole can take any other shape, such as square, hexagon, or the like. For this purpose, it is preferable that the X-ray alignment member be a thin plate.

FIG. 25 schematically shows a positional relation between the holes in the X-ray alignment member and the pinhole member. If the holes in each of the upper and lower alignment plates $500_1$ and $500_2$ are formed an equal pitch, and the coordinates of the centers of the corresponding holes in the upper and lower plates have a proportional relationship (i.e., proportional enlargement or reduction), then X-rays 103 passed through the two alignment plates will converge onto a single point. This can be proved geometrically as shown in FIGS. 26 and 27.

FIG. 26 is a schematic illustration of a part of FIG. 25. First, let C be the point at which radiation AB and DE intersect. Let us prove that the extension of EG passes through C in FIG. 25. ADF and BEG are parallel to each other, and AD=DF and BE=EG. Let G' be the point at which the line connecting F and C intersects the lower alignment plate $500_2$. Then, it is required to prove that G' coincides with G. The triangle CDF and the triangle CEG' are similar to each other. Thus, since AD=DF, BE=EG'. From the equal pitch assumption, BE=EG. Thus, EG=BE=EG'. It was thus proved that G' coincides with G.

Although FIG. 25 is shown one-dimensionally, the above proof likewise holds for two dimensions. In practice, the upper and lower alignment plates are two-dimensional. A large number of beams of X-rays that converge onto a single point are distributed two-dimensionally.

FIG. 28 is an enlarged view of part of FIGS. 2A to 2C. In FIG. 28, a beam of X-rays X1 passes through the object and reaches the storage type image sensor while undergoing absorption at points B1, B2, B3, . . . , A, . . . , E4, E3, E2, E1. Assuming that, in this process, very strong absorption occurs at point B3, a tomographic image value in the vicinity of the B3 point in a specific slice S11 of the object 100 will be affected. In FIG. 28 there is illustrated the effect of the point B3 on signal values with coordinate positions in the direction of travel of the object as the axis of abscissa and image signal values as the axis of ordinate. When the absorption is small, the signal value becomes large and vice versa. Even an image signal value at point A at which beams of X-rays X1, X2, X3, X4, X5, . . . , XN (N is a large number) pass through may be affected by the absorption at point B3.

The point B3 have an effect on all portions in the vicinity of B3. The reason is that X-rays passing through B3 exist over the range of at least 50 degrees or more. Thus, the effect of B3 appears as low frequency components (not sufficiently averaged) in an electronic waveform. When a highpass filtering process is performed on the waveform, a signal waveform as expressed in FIG. 28 as an image signal having low frequency components removed results. Thus, the effect of point B3 is minimized.

As an example, when the object is a human body and tomographic images are observed to identify the diseased part and judge the conditions of that part, it is often desired that the tomographic images look stereoscopic. In imaging diagnosis of a specific internal organ, it is preferable that images before and behind that organ look lightly superimposed upon each other to provide stereoscopic vision. This will make it easy to judge the relationship between the organ and the surrounding region, providing good visibility.

On the other hand, the CT is, in principle, adapted to produce only an image of a plane section of a body and thus provides no information in the direction of depth. In order to produce a stereoscopic image, therefore, it must be produced from a plurality of images for plane sections of the body, requiring lengthy calculations. In addition, it is difficult to